United States Patent
Zhang

(10) Patent No.: US 9,550,738 B2
(45) Date of Patent: Jan. 24, 2017

(54) BICYCLIC COMPOUNDS AS KINASES INHIBITORS

(71) Applicant: HangzhouDeRenYuCheng Biotechnology Ltd, Hangzhou (CN)

(72) Inventor: Dawei Zhang, Thousand Oaks, CA (US)

( * ) Notice: Subject to any disclaimer, the term of this patent is extended or adjusted under 35 U.S.C. 154(b) by 0 days.

(21) Appl. No.: 14/401,108

(22) PCT Filed: May 13, 2013

(86) PCT No.: PCT/US2013/040825
§ 371 (c)(1),
(2) Date: Nov. 13, 2014

(87) PCT Pub. No.: WO2013/173254
PCT Pub. Date: Nov. 21, 2013

(65) Prior Publication Data
US 2015/0126537 A1 May 7, 2015

Related U.S. Application Data

(60) Provisional application No. 61/688,736, filed on May 14, 2012.

(51) Int. Cl.
*A61K 31/517* (2006.01)
*C07D 239/86* (2006.01)
*C07D 403/12* (2006.01)
*C07D 407/12* (2006.01)
*C07D 239/94* (2006.01)
*C07D 401/12* (2006.01)
*C07D 405/12* (2006.01)

(52) U.S. Cl.
CPC .......... *C07D 239/94* (2013.01); *C07D 401/12* (2013.01); *C07D 405/12* (2013.01)

(58) Field of Classification Search
CPC .... C07D 239/86; C07D 403/12; C07D 407/12
See application file for complete search history.

(56) References Cited

U.S. PATENT DOCUMENTS

| 6,127,374 A * | 10/2000 | Bridges ............... C07D 239/74 514/217.06 |
| 7,547,781 B2 | 6/2009 | Qian |
| 7,585,869 B2 * | 9/2009 | Bhattacharya et al. . 514/266.22 |
| 2010/0240649 A1 | 9/2010 | Zhang |

FOREIGN PATENT DOCUMENTS

| AU | WO2004031232 A1 | 4/2004 |
| WO | WO2010151710 A2 | 12/2010 |
| WO | WO2013053206 A1 | 4/2013 |

OTHER PUBLICATIONS

Smaill et al. Tyrosine kinase inhibitors. 15. 4-(Phenylamino)quinazoline and 4-(phenylamino)pyrido[d]pyrimidine acrylamides as irreversible inhibitors of the ATP binding site of the epidermal growth factor receptor, Journal of Medicinal Chemistry, 1999, 42, 1803-1815).*

* cited by examiner

*Primary Examiner* — Brian McDowell
(74) *Attorney, Agent, or Firm* — Feng Tian

(57) ABSTRACT

The present invention is directed to novel bicyclic compounds, their derivatives, pharmaceutically acceptable salts, solvates and hydrates thereof. The compounds and compositions of the present invention have protein kinases inhibitory activities and are useful for the treatment of protein kinases mediated diseases and conditions. Novel bicyclic compounds disclosed herein include quinazolines shown in Formula I (X=N).

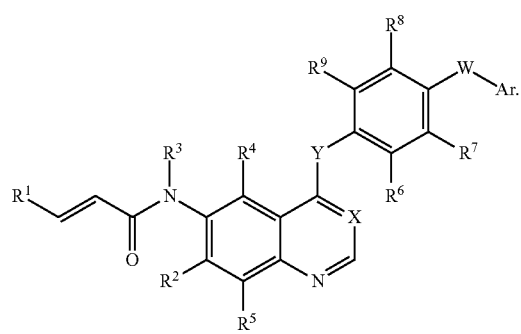

10 Claims, No Drawings

BICYCLIC COMPOUNDS AS KINASES INHIBITORS

CROSS REFERENCE TO RELATED APPLICATION

The application is a 35 U.S.C. §371 national stage filing of International Patent Application PCT/US2013/040825 (published as WO 2013/173254 A1), filed May 13, 2013, which is entitled to priority pursuant to 35 U.S.C. §119(e) to U.S. Provisional Application No. 61/688,736, filed May 14, 2012. The entire disclosures of the afore-mentioned patents are hereby incorporated by reference in their entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Due to their activity in numerous cellular processes, protein kinases have emerged as important therapeutic targets.

Bruton's tyrosine kinase (Btk) plays a key role in promoting B cell proliferation and survival through participation in the B cell receptor (BCR) signaling pathway and represents a promising new drug target. Targeted therapies that suppress BCR signaling have emerged as promising agents in the treatment of several B cell malignancies. To this end, attempts have been made to identify small molecules which act as Btk inhibitors. For example, patent U.S. Pat. No. 7,982,036 describes 4,6-disubstituted pyrimidine compounds as useful kinase inhibitors targeting the Tec kinase family. The disclosed compounds include Btk inhibitors. Another class of Btk inhibitors has been disclosed in patent U.S. Pat. No. 8,088,781.

Thus, the compounds that can inhibit protein kinases such as Bruton's tyrosine kinase (Btk) activity are highly desired.

SUMMARY OF THE INVENTION

In some embodiments of the present invention, there are provided compounds of Formula I:

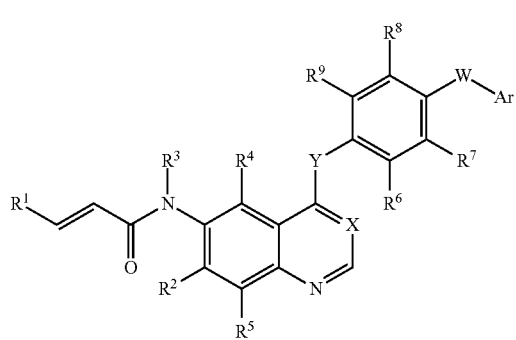

I or a pharmaceutically acceptable salt, solvate or a prodrug or a stereoisomer or a tautomer or a metabolite thereof, wherein
X is CH or N;
Y is O, S, or NH;
W is $CHR^3$, O, S, NH, C(O), S(O), or $S(O)_2$;
Ar is $C_6$-$C_{12}$ aryl, 5-12 membered heteroaryl, $C_3$-$C_{12}$ cycloalkyl, or 3-12 membered heteroalicyclic, and Ar is optionally substituted by one or more $R^{10}$ groups;
$R^1$ is hydrogen, $-(CHR^3)_m N(O)R^{11}R^{12}$, $-(CHR^3)_m NR^{11}R^{12}$, or $-(CHR^3)_m R^{13}$;
$R^2$ is hydrogen, $C_1$-$C_6$ alkyl, F, Cl, CN, $CF_3$, or $OR^{14}$;
each $R^3$ is independently hydrogen or $C_1$-$C_6$ alkyl;
$R^4$, $R^5$, $R^6$, $R^7$, $R^8$ and $R^9$ are independently hydrogen, $C_1$-$C_6$ alkyl, $C_1$-$C_6$ alkoxy, F, Cl, CN, or $CF_3$;
each $R^{10}$ is independently halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, $-NR^{15}R^{16}$, $-(CR^{17}R^{18})_n OR^{15}$, $-CN$, $-C(O)R^{15}$, $-O(CO)R^{15}$, $-O(CR^{17}R^{18})_n R^{15}$, $-OCR^{17}R^{18}(CR^{17}R^{18})_n NR^{15}R^{16}$, $-OCR^{17}R^{18}(CR^{17}R^{18})_n OR^{15}$, $-NR^{15}C(O)R^{16}$, $-(CR^{17}R^{18})_n C(O)OR^{15}$, $-(CR^{17}R^{18})_n C(O)NR^{15}R^{16}$, $-(CR^{17}R^{18})_n NR^{15}R^{16}$, $-NR^{15}(CO)NR^{15}R^{16}$, $-NR^{15}S(O)_p R^{16}$, $-C(O)NR^{15}$, $-S(O)_t R^{15}$, or $-S(O)_2 NR^{15}R^{16}$, wherein two $R^{10}$ groups on adjacent atoms of Ar may, together with the adjacent atoms to which two $R^{10}$ groups are bound, be combined to form a $C_6$-$C_{12}$ aryl, 5-12 membered heteroaryl, $C_3$-$C_{12}$ cycloalkyl or 3-12 membered heteroalicyclic;
$R^{11}$ and $R^{12}$ are independently hydrogen, $C_1$-$C_6$ alkyl, or $-CR^{17}R^{18}(CR^{17}R^{18})_n OR^{15}$;
$R^{13}$ is morpholine, piperidine, piperazine, piperazine-N ($C_1$-$C_6$ alkyl), or pyrrolidine, and each hydrogen in $R^{13}$ is optionally substituted by one or more $C_1$-$C_6$ alkyl, $C_1$-$C_6$ alkoxy, halogen, OH, $NH_2$, $NH(C_1$-$C_6$ alkyl), or $N(C_1$-$C_6$ alkyl)$_2$;
$R^{14}$ is $C_1$-$C_6$ alkyl, $-CR^{17}R^{18}(CR^{17}R^{18})_n OR^{15}$, tetrahydrofuran-3-yl, $-(CH_2)_m$-morpholine, $-(CH_2)_m$-piperidine, or $-(CH_2)_m$-piperazine-N($C_1$-$C_3$ alkyl);
each $R^{15}$, $R^{16}$, $R^{17}$, and $R^{18}$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^{15}$, $R^{16}$, $R^{17}$, and $R^{18}$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^{15}$, $R^{16}$, $R^{17}$, and $R^{18}$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;
each m is independently 1, 2, or 3;
each n is independently 0, 1, 2, 3, or 4;
each p is independently 1 or 2;
each t is independently 0, 1, or 2;
with the proviso that the compound is not N-(4-((4-phenoxyphenyl)amino)quinazolin-6-yl)acrylamide or N-(4-((4-benzoylphenyl)amino)quinazolin-6-yl)acrylamide.

The present invention further provides pharmaceutical compositions comprising a compound of Formula I described above and a pharmaceutically acceptable carrier.

The present invention further provides methods for regulating the kinase signaling transduction comprising administrating to a mammalian subject a therapeutically effective amount of any of the compounds of Formula I described above.

DETAILED DESCRIPTION OF THE INVENTION

In some embodiments of the present invention, there are provided compounds of Formula I:

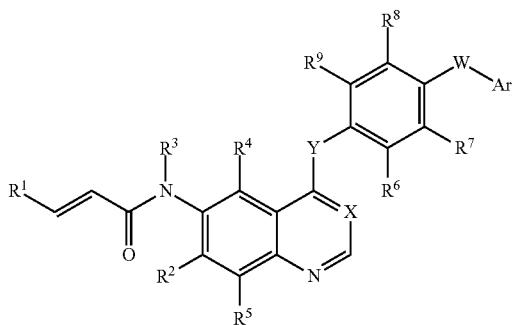

I or a pharmaceutically acceptable salt, solvate or a prodrug or a stereoisomer or a tautomer or a metabolite thereof, wherein X is CH or N;
Y is O, S, or NH;
W is $CHR^3$, O, S, NH, C(O), S(O), or $S(O)_2$;
Ar is $C_6$-$C_{12}$ aryl, 5-12 membered heteroaryl, $C_3$-$C_{12}$ cycloalkyl, or 3-12 membered heteroalicyclic, and Ar is optionally substituted by one or more $R^{10}$ groups;
$R^1$ is hydrogen, $-(CHR^3)_m N(O)R^{11}R^{12}$, $-(CHR^3)_m NR^{11}R^{12}$, or $-(CHR^3)_m R^{13}$;
$R^2$ is hydrogen, $C_1$-$C_6$ alkyl, F, Cl, CN, $CF_3$, or $OR^{14}$;
each $R^3$ is independently hydrogen or $C_1$-$C_6$ alkyl;
$R^4$, $R^5$, $R^6$, $R^7$, $R^8$ and $R^9$ are independently hydrogen, $C_1$-$C_6$ alkyl, $C_1$-$C_6$ alkoxy, F, Cl, CN, or $CF_3$;
each $R^{10}$ is independently halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, $-NR^{15}R^{16}$, $-(CR^{17}R^{18})_n OR^{15}$, CN, $-C(O)R^{15}$, $-O(CO)R^{15}$, $-O(CR^{17}R^{18})_n R^{15}$, $-OCR^{17}R^{18}(CR^{17}R^{18})_n NR^{15}R^{16}$, $-OCR^{17}R^{18}(CR^{17}R^{18})_n OR^{15}$, $-NR^{15}C(O)R^{16}$, $-(CR^{17}R^{18})_n C(O)OR^{15}$, $-(CR^{17}R^{18})_n C(O)NR^{15}R^{16}$, $-(CR^{17}R^{18})_n NR^{15}R^{16}$, $-NR^{15}(CO)NR^{15}R^{16}$, $-NR^{15}S(O)_p R^{16}$, $-C(O)NR^{15}$, $-S(O)_t R^{15}$, or $-S(O)_2 NR^{15}R^{16}$, wherein two $R^{10}$ groups on adjacent atoms of Ar may, together with the adjacent atoms to which two $R^{10}$ groups are bound, be combined to form a $C_6$-$C_{12}$ aryl, 5-12 membered heteroaryl, $C_3$-$C_{12}$ cycloalkyl or 3-12 membered heteroalicyclic;
$R^{11}$ and $R^{12}$ are independently hydrogen, $C_1$-$C_6$ alkyl, or $-CR^{17}R^{18}(CR^{17}R^{18})_n OR^{15}$;
$R^{13}$ is morpholine, piperidine, piperazine, piperazine-N($C_1$-$C_6$ alkyl), or pyrrolidine, and each hydrogen in $R^{13}$ is optionally substituted by one or more $C_1$-$C_6$ alkyl, $C_1$-$C_6$ alkoxy, halogen, OH, $NH_2$, NH($C_1$-$C_6$ alkyl), or N($C_1$-$C_6$ alkyl)$_2$;
$R^{14}$ is $C_1$-$C_6$ alkyl, $-CR^{17}R^{18}(CR^{17}R^{18})_n OR^{15}$, tetrahydrofuran-3-yl, $-(CH_2)_m$-morpholine, $-(CH_2)_m$-piperidine, or $-(CH_2)_m$-piperazine-N($C_1$-$C_3$ alkyl);
each $R^{15}$, $R^{16}$, $R^{17}$, and $R^{18}$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^{15}$, $R^{16}$, $R^{17}$, and $R^{18}$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^{15}$, $R^{16}$, $R^{17}$, and $R^{18}$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;
each m is independently 1, 2, or 3;
each n is independently 0, 1, 2, 3, or 4;
each p is independently 1 or 2;
each t is independently 0, 1, or 2;
with the proviso that the compound is not N-(4-((4-phenoxyphenyl)amino)quinazolin-6-yl)acrylamide or N-(4-((4-benzoylphenyl)amino)quinazolin-6-yl)acrylamide.

In some embodiments of the present invention, there are provided compounds of Formula II:

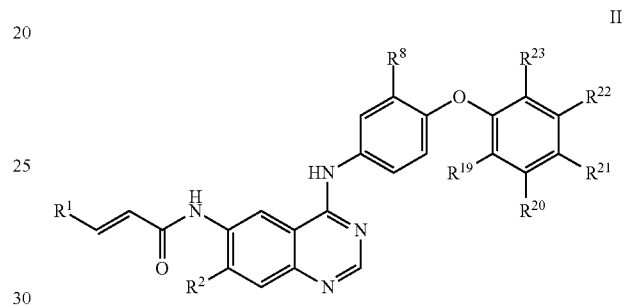

II or a pharmaceutically acceptable salt, solvate or a prodrug or a stereoisomer or a tautomer or a metabolite thereof, wherein
$R^1$ is hydrogen, $-(CHR^3)_m N(O)R^{11}R^{12}$, $-(CHR^3)_m NR^{11}R^{12}$, or $-(CHR^3)_m R^{13}$;
$R^2$ is hydrogen, $C_1$-$C_6$ alkyl, F, Cl, CN, $CF_3$, or $OR^{14}$;
each $R^3$ is independently hydrogen or $C_1$-$C_6$ alkyl;
$R^8$ is hydrogen, $C_1$-$C_6$ alkyl, $C_1$-$C_6$ alkoxy, F, Cl, CN, or $CF_3$;
$R^{11}$ and $R^{12}$ are independently hydrogen, $C_1$-$C_6$ alkyl, or $-CR^{17}R^{18}(CR^{17}R^{18})_n OR^{15}$;
$R^{13}$ is morpholine, piperidine, piperazine, piperazine-N($C_1$-$C_6$ alkyl), or pyrrolidine, and each hydrogen in $R^{13}$ is optionally substituted by one or more $C_1$-$C_6$ alkyl, $C_1$-$C_6$ alkoxy, halogen, OH, $NH_2$, NH($C_1$-$C_6$ alkyl), or N($C_1$-$C_6$ alkyl)$_2$;
$R^{14}$ is $C_1$-$C_6$ alkyl, $-CR^{17}R^{18}(CR^{17}R^{18})_n OR^{15}$, tetrahydrofuran-3-yl, $-(CH_2)_m$-morpholine, $-(CH_2)_m$-piperidine, or $-(CH_2)_m$-piperazine-N($C_1$-$C_3$ alkyl);
each $R^{15}$, $R^{16}$, $R^{17}$, and $R^{18}$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^{15}$, $R^{16}$, $R^{17}$, and $R^{18}$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^{15}$, $R^{16}$, $R^{17}$, and $R^{18}$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;
each $R^{19}$, $R^{20}$, $R^{21}$, $R^{22}$ and $R^{23}$ is independently hydrogen, halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, $-NR^{15}R^{16}$, $-(CR^{17}R^{18})_n OR^{15}$, CN, $-C(O)R^{15}$, $-O(CO)R^{15}$, —O(CR$^{17}$R$^{18}$)$_n$R$^{15}$, —OCR$^{17}$R$^{18}$(CR$^{17}$R$^{18}$)$_n$NR$^{15}$R$^{16}$, —OCR$^{17}$R$^{18}$(CR$^{17}$R$^{18}$)$_n$OR$^{15}$, —NR$^{15}$C(O)R$^{16}$, —(CR$^{17}$R$^{18}$)$_n$C(O)OR$^{15}$, —(CR$^{17}$R$^{18}$)$_n$C(O)NR$^{15}$R$^{16}$, —(CR$^{17}$R$^{18}$)$_n$NR$^{15}$R$^{16}$, —NR$^{15}$(CO)—NR$^{15}$R$^{16}$, —NR$^{15}$S(O)$_p$R$^{16}$—C(O)NR$^{15}$, —S(O)$_t$R$^{15}$, —S(O)$_2$NR$^{15}$R$^{16}$, and R$^{16}$ groups on adjacent atoms may combine to form a C$_6$-C$_{12}$ aryl, 5-12 membered heteroaryl, C$_3$-C$_{12}$ cycloalkyl or 3-12 membered heteroalicyclic;

each m is independently 1, 2, or 3;
each n is independently 0, 1, 2, 3, or 4;
each p is independently 1 or 2;
each t is independently 0, 1, or 2;
with the proviso that the compound is not N-(4-((4-phenoxyphenyl)amino)quinazolin-6-yl)acrylamide.

In certain embodiments, R$^1$ is hydrogen. In some embodiments, R$^1$ is N,N-dimethylaminomethyl. In other embodiments, R$^2$ is hydrogen. In some embodiments, R$^2$ is methoxy or ethoxy. In other embodiments R$^3$ is hydrogen. In certain embodiments, R$^4$, R$^5$, R$^6$, R$^7$, R$^8$, or R$^9$ is hydrogen. In some embodiments, Ar is phenyl. In other embodiments, X is N and Y is NH. In certain embodiments, R$^8$, R$^{19}$, R$^{20}$, R$^{21}$, R$^{22}$, and R$^{23}$ are independently hydrogen or halogen. In other embodiments, the compound of Formulas I-II is in the form of pharmaceutically acceptable salt. In some embodiments, the compound of Formula I-II is in the form of a solvate. In other embodiments, the compound of Formulas I-II is in the form of a metabolite. In other embodiments, the compound of Formulas I-II is in the form of a prodrug. In some embodiments, the compound of Formulas I-II is a stereoisomer. In other embodiments, the compound of Formulas I-II is a tautomer. In another embodiment, the deuterium enrichment in compounds of Formulas I-II is at least about 1%.

In certain embodiments, there are provided compounds without limitation selected from the group consisting of:
(E)-4-(dimethylamino)-N-(7-methoxy-4-((4-phenoxyphenyl)amino)quinazolin-6-yl)but-2-enamide;
(E)-4-(dimethylamino)-N-(7-ethoxy-4-((4-phenoxyphenyl)amino)quinazolin-6-yl)but-2-enamide;
(S,E)-4-(dimethylamino)-N-(4-((4-phenoxyphenyl)amino)-7-((tetrahydrofuran-3-yl)oxy)quinazolin-6-yl)but-2-enamide;
(E)-4-(dimethylamino)-N-(4-((4-(4-fluorophenoxy)phenyl)amino)-7-methoxyquinazolin-6-yl)but-2-enamide;
(E)-N-(4-((4-(3-cyanophenoxy)phenyl)amino)-7-methoxyquinazolin-6-yl)-4-(dimethylamino)but-2-enamide;
(E)-4-(dimethylamino)-N-(7-methoxy-4-((4-(3-trifluoromethyl)phenoxy)phenyl)amino)quinazolin-6-yl)but-2-enamide;
(E)-4-(dimethylamino)-N-(7-methoxy-4-((4-(pyridin-2-yloxy)phenyl)amino)quinazolin-6-yl)but-2-enamide;
(E)-N-(4-((4-(3,4-dichlorophenoxy)phenyl)amino)-7-methoxyquinazolin-6-yl)-4-(dimethylamino)but-2-enamide;
(E)-4-(diethylamino)-N-(7-methoxy-4-((4-phenoxyphenyl)amino)quinazolin-6-yl)but-2-enamide;
(E)-4-(diethylamino)-N-(4-((4-phenoxyphenyl)amino)quinazolin-6-yl)but-2-enamide;
(E)-N-(4-((4-phenoxyphenyl)amino)quinazolin-6-yl)-4-(piperidin-1-yl)but-2-enamide;
(E)-N-(7-methoxy-4-((4-phenoxyphenyl)amino)quinazolin-6-yl)-4-(piperidin-1-yl)but-2-enamide;
N-(7-methoxy-4-((4-phenoxyphenyl)amino)quinazolin-6-yl)acrylamide;
N-(7-ethoxy-4-((4-phenoxyphenyl)amino)quinazolin-6-yl)acrylamide;
(S)-N-(4-((4-phenoxyphenyl)amino)-7-((tetrahydrofuran-3-yl)oxy)quinazolin-6-yl)acrylamide, and the like, or a pharmaceutically acceptable salt, solvate, or a prodrug, or a metabolite thereof. In some embodiments, there are provided pharmaceutical compositions comprising a compound of Formula I or II and a pharmaceutically acceptable carrier. In certain embodiments, the compositions are for the treatment of a disease regulated by a protein kinase. In certain embodiments, the compositions are for or the treatment of a hyper-proliferative disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present invention provides methods for regulating the kinase signaling transduction, said methods comprising administrating to a mammalian subject a therapeutically effective amount of a compound of Formula I or II.

In other embodiments, there are provided herein methods for treating or preventing a Bruton's tyrosine kinase (Btk) mediated disorder, said method comprising administrating to a mammalian subject a therapeutically effective amount of a compound of Formula I.

In yet another aspect, there are provided herein methods for inhibiting human epidermal growth factor receptor (HER) kinases, said methods comprising administrating to a mammalian subject a therapeutically effective amount of a compound of Formula I or II. In other embodiments, there are provided herein methods for treating neoplasia, said methods comprising administrating to a mammalian subject in need of treatment, a therapeutically effective amount of a compound of Formula I or II. In certain embodiments, the neoplasia is selected from B cell malignancies, liver cancer, skin cancer, leukemia, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer and prostate cancer. In certain embodiments, chronic lymphocytic leukemia, mantle cell lymphoma, diffuse large B-cell lymphoma, and multiple myeloma, breast cancer or the lung cancer.

Definitions

The term "alkyl" is intended to include straight, branched, and cyclic hydrocarbon groups, which contain only single carbon-carbon bonds and which may be unsubstituted or optionally substituted with one or more functional groups. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. The preferred chain length of an alkyl group is from 1 to 6 carbon atoms. C$_1$-C$_6$ alkyl is intended to include C$_1$, C$_2$, C$_3$, C$_4$, C$_5$ and C$_6$ alkyl groups. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^X$R$^Y$, wherein R$^X$ and R$^Y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Illustrative substituted alkyl group include, but are not limited to, fluoromethyl, difluoromethyl, trifluoromethyl, hydoxymethyl, methoxymethyl, 2-fluoroethyl, 2-methoxyethyl, etc.

The term "alkoxy" refers to both an —O-(alkyl) or an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

"Cycloalkyl" refers to a 3 to 8 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

"Aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^XR^Y$, with $R^X$ and $R^Y$ as defined above.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrazine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^XR^Y$ with $R^X$ and $R^Y$ as defined above. A pharmaceutically acceptable heteroaryl is one that is sufficiently stable to be attached to a compound of the invention, formulated into a pharmaceutical composition and subsequently administered to a patient in need thereof.

"Heteroalicyclic" or "heterocycle" refers to a monocyclic or fused ring group having in the ring(s) of 3 to 12 ring atoms, in which one or two ring atoms are heteroatoms selected from N, O, and $S(O)_t$ (where t is 0, 1 or 2), the remaining ring atoms being C. The rings may also have one or more double bonds. However, the rings do not have a completely conjugated π-electron system. Additionally, one or more of the ring atoms could be substituted by an oxo group. Examples of suitable saturated heteroalicyclic groups include, but are not limited to: tetrahydrofuran, tetrahydrothiophene, pyrrolidine, piperidine, morpholine, piperazine, "Halogen" means fluorine, chlorine, bromine, and iodine. "Halo" means fluoro, chloro, bromo, and iodo, preferably fluorine or chlorine.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}C$. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "comprising" is meant to be open-ended, including the indicated component(s), but not excluding other elements.

The term "pharmaceutically acceptable" when used with reference to a compound of Formulas I-II is intended to refer to a form of the compound that is safe for administration to a subject. For example, a free base, a salt form, a solvate, a hydrate, a prodrug or derivative form of a compound of Formulas I-II, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I-II are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formulas I-II are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973), T. W. Greene and P. G. M. Wuts, *Protective Groups in Organic Synthesis*, Wiley, 3$^{rd}$ edition, John Wiley and Sons (1999), E. Gross and J. Meienhofer, *The Peptides*, Volume 3, Academic Press, London and New York (1981).

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Indication

The present invention provides compounds which are capable of modulating one or more signal transduction pathways comprising, but not limited to Bruton's tyrosine kinase (Btk). By the term "modulate," it is meant that the functional activity of the pathway (or a component thereof) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention may also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Combinations

While the compounds of the invention can be dosed or administered as the sole active pharmaceutical agent, they can also be used in combination with one or more compounds of the invention or in conjunction with other agents.

When administered as a combination, the therapeutic agents can be formulated as separate compositions that are administered simultaneously or sequentially at different times, or the therapeutic agents can be given as a single composition.

In some embodiments, methods for treatment of androgen receptor-dependent or androgen receptor-mediated conditions or diseases, such as proliferative disorders, including cancer, comprises administration to a mammal a compound of Formulas I-II in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

Specifically, the administration of compounds of the present invention in some embodiments are in conjunction with additional therapies known to those skilled in the art in the prevention or treatment of cancer. The foregoing description is merely illustrative of the invention and is not intended to limit the invention to the disclosed compounds, compositions and methods.

Synthesis of Compounds

The compounds of Formulas I-II were synthesized according to the procedures described in the following Schemes to those skilled in the art, wherein the substituents are as defined for Formulas I-II above, except where further noted. The synthetic methods described below are merely exemplary, and the compounds of the invention may also be synthesized by alternate routes as appreciated by persons of ordinary skill in the art. Compound 1 and compound 2 are commercial available, literature known or were prepared readily by following similar literature known procedures. The reaction of compound 1 and compound 2 in alcohol such as isopropyl alcohol can lead to the synthesis of compound 3. The nitro group of compound 3 was reduced to the amino group with metal such as iron to generate compound 4. (*Tetrahedron Letters*, 42(46), 8141-8142; 2001; *Faming Zhuanli Shenqing Gongkai Shuomingshu*, 1313274, 19 Sep. 2001). The amino group of compound 4 was alkylated to give compound 5 (where $R^3$ is not hydrogen). The acylation of compound 5 with compound 6 led to the preparation of compound 7 described in Formula I (Scheme 1).

Scheme 1

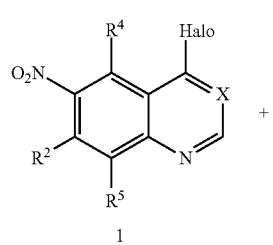

1

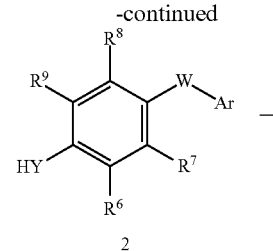

2

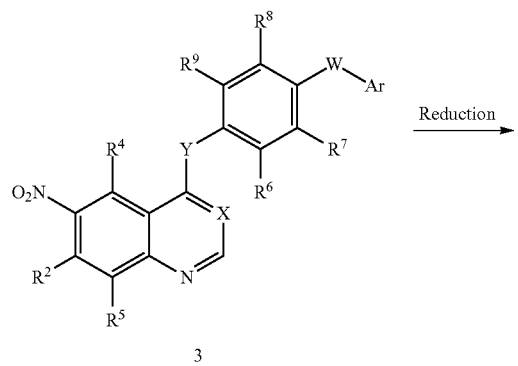

3

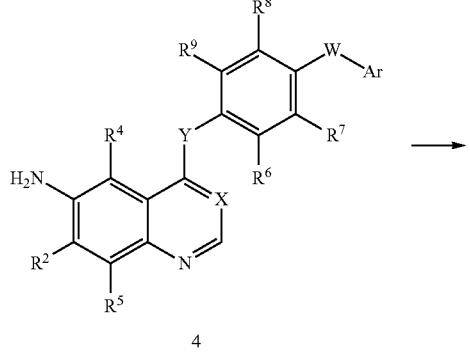

4

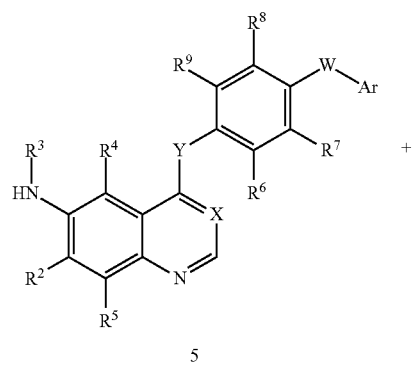

5

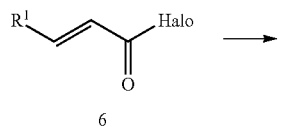

6

Scheme 3

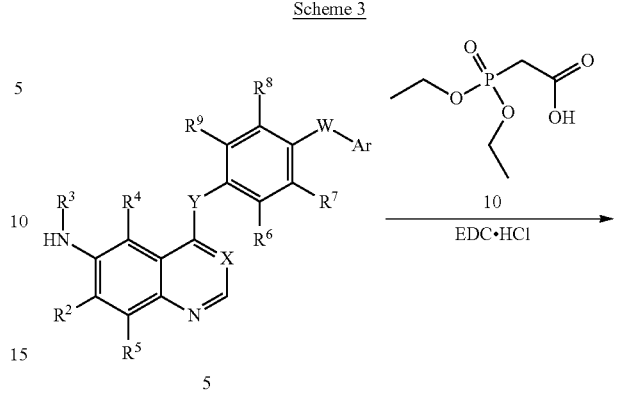

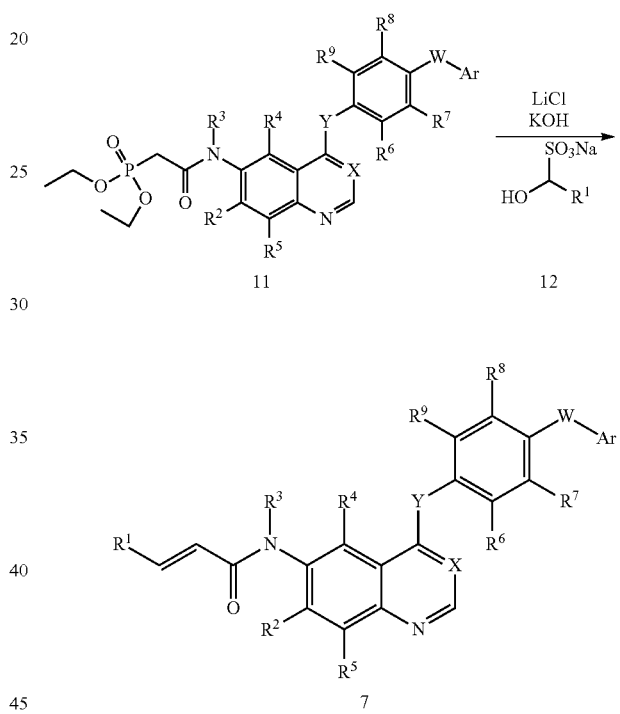

An alternative preparation of compound 3 (wherein $R^2$ is $OR^{14}$) is described in Scheme 2. The reaction between compounds 8 and 2 led to the preparation of compound 9. The halo group of compound 9 was replaced by $R^2$ to afford compound 3.

Scheme 2

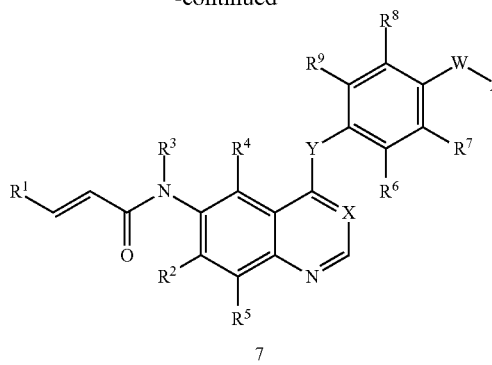

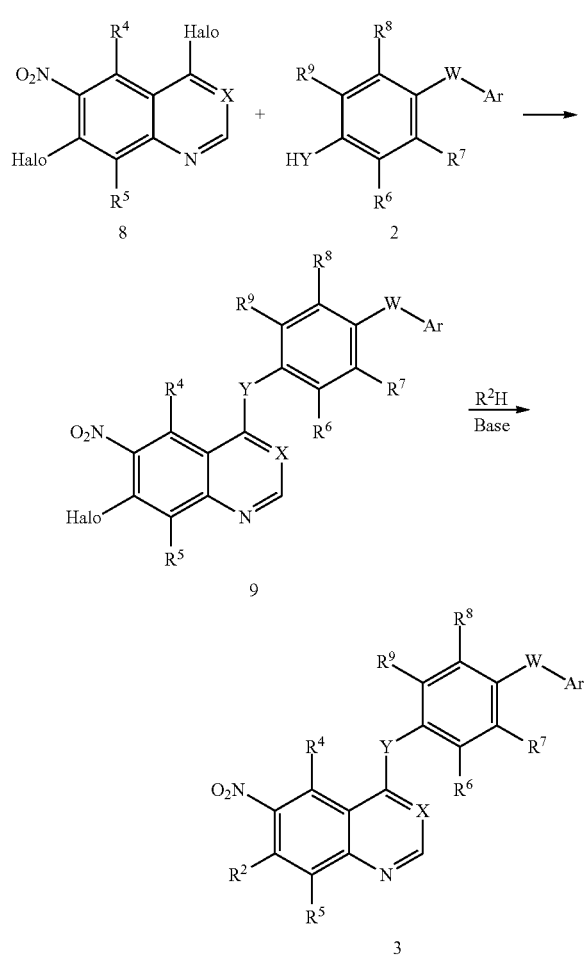

An alternative preparation of compound 7 is described in Scheme 3. The coupling reaction of compound 5 with 2-(diethoxyphosphoryl)acetic acid (compound 10) led to the synthesis of compound 11, which reacted further with compound 12 to afford compound 7.

The synthesis of compound 18 in Formula II is described in Scheme 4. Compound 13 or compound 14 is commercial available, literature known or was prepared readily by following a literature known procedure on similar analogs. The replacement of chloride in compound 13 by the amino group in compound 14 in alcohol such as isopropyl alcohol afforded compound 15. The reduction of nitro group of compound 15 to yield compound 16, which was acylated by compound 17 to afford compound 18 in Formula II.

Scheme 4

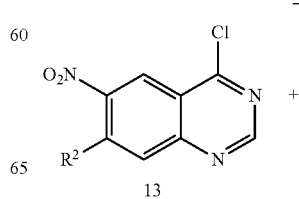

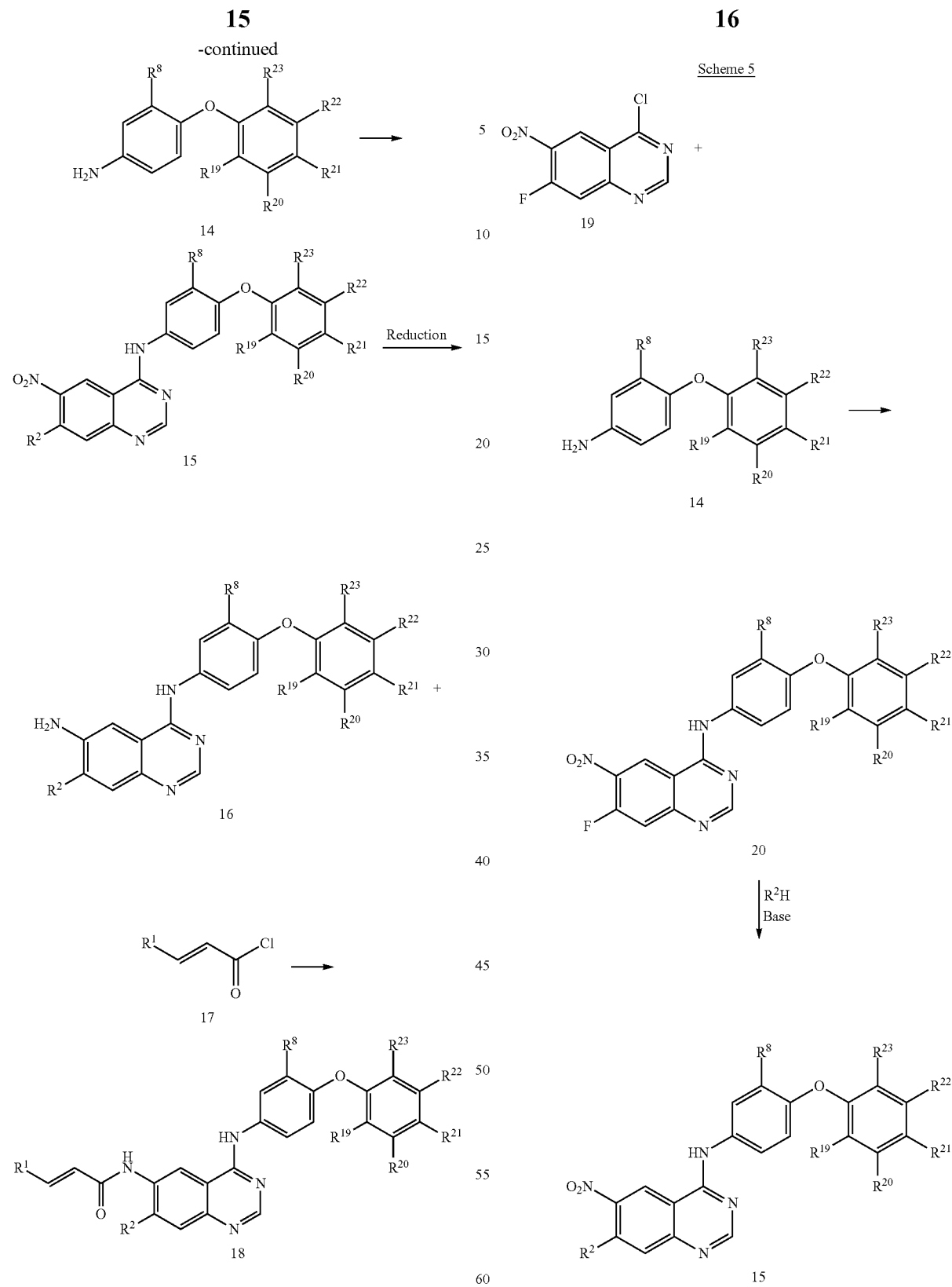

Scheme 5

An alternative preparation of compound 15 (wherein $R^2$ is $OR^{14}$ i) is described in Scheme 5. The reaction between compound 19 and 14 led to the preparation of compound 20. The fluoride group of compound 20 was replaced by $R^2H$ and bases, such as, sodium hydride or potassium tert-butoxide, to afford compound 15.

An alternative preparation of compound 18 is described in Scheme 6. The coupling reaction of compound 16 with 2-(diethoxyphosphoryl)acetic acid (compound 10) led to the synthesis of compound 21, which reacted further with compound 12 to afford compound 18 in Formula II.

Scheme 6

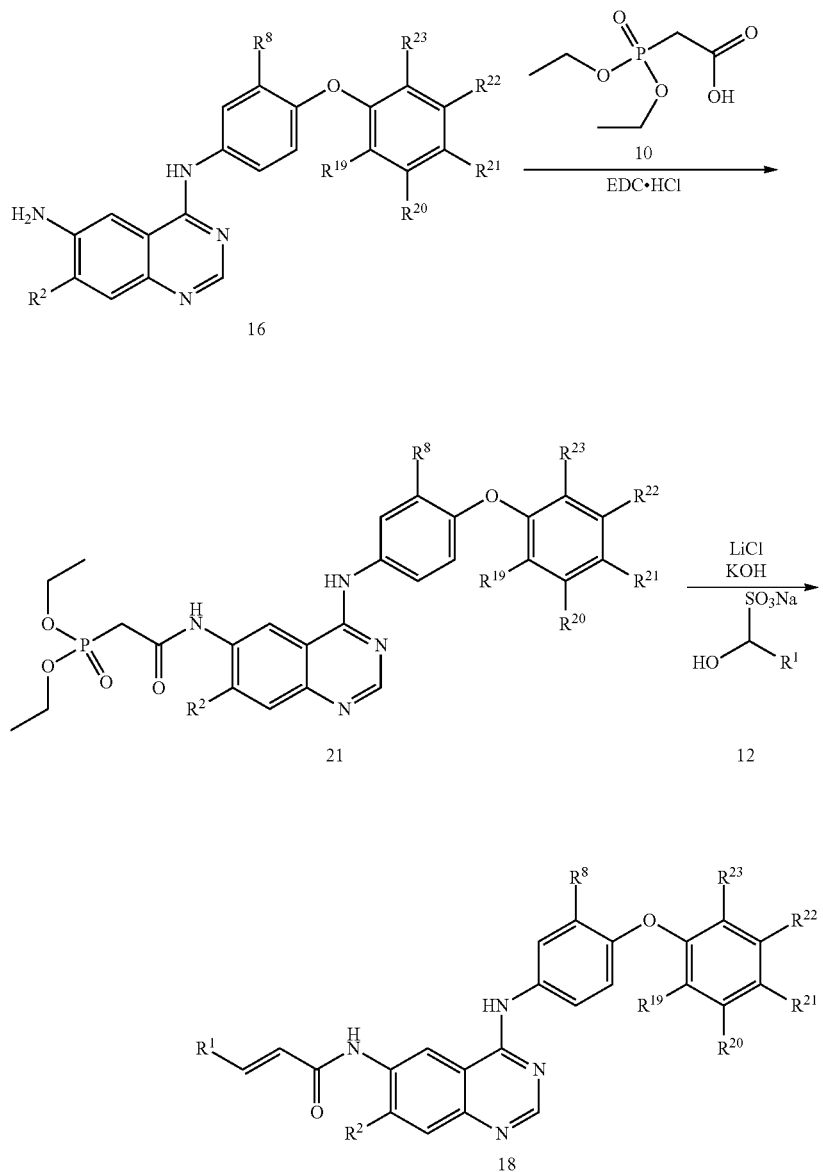

The preparation of compound 19-27 is described in Scheme 7. The reaction between compound 19 and compound 22 in isopropyl alcohol afforded compound 23. Replacement of fluoro group of compound 23 by methoxy group to generate compound 24. The reduction of nitro group of compound 24 yielded compound 25, which reacted with compound 10 to give compound 26. The reaction of compound 26 and compound 13 led to the preparation of compound 27.

Scheme 7

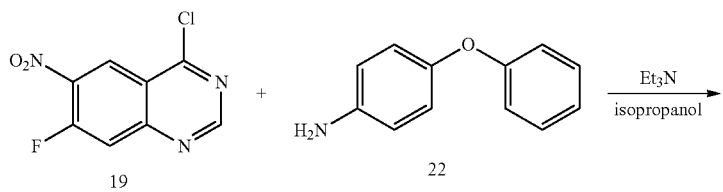

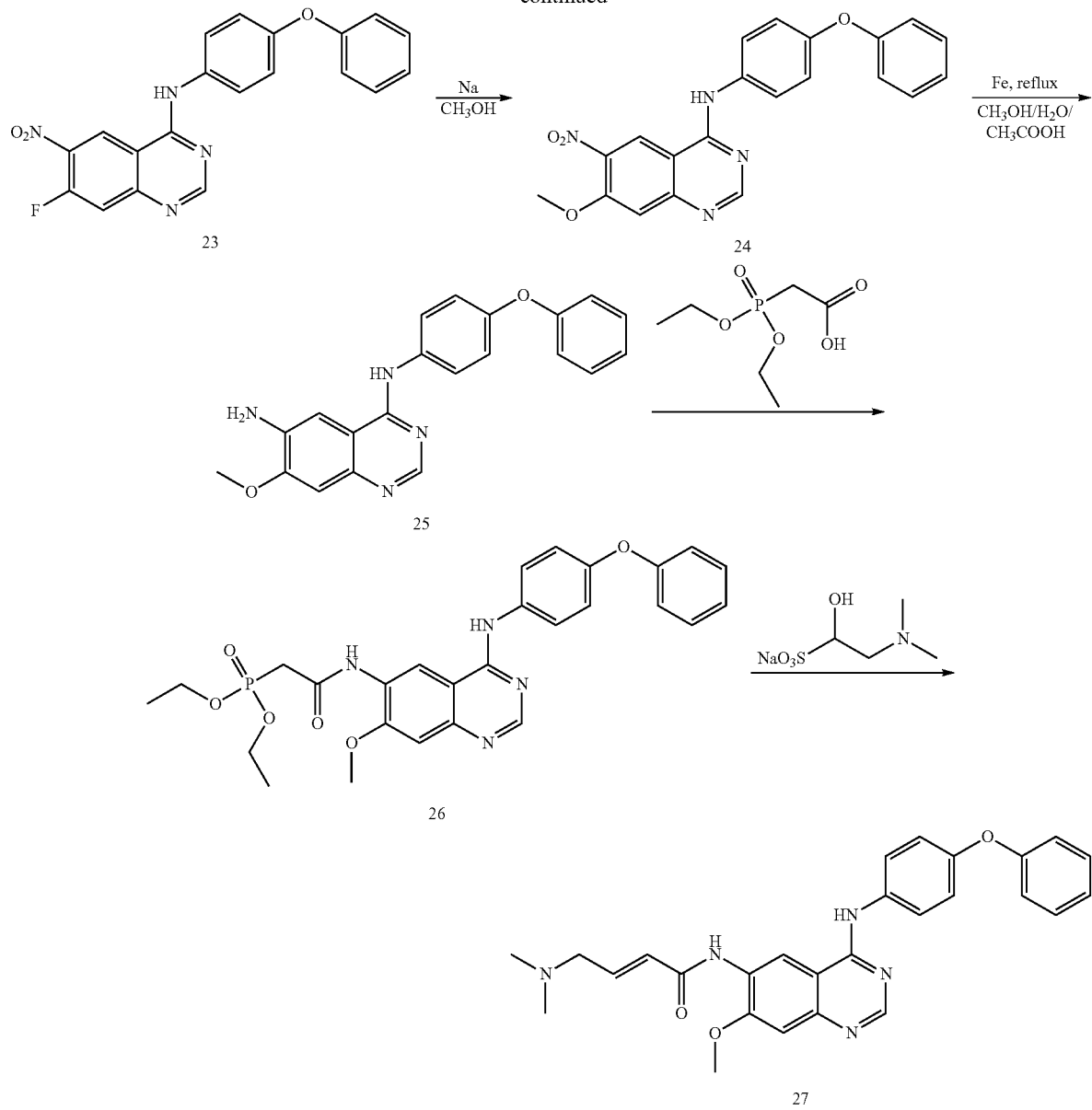
The synthesis of compound 31(Scheme 8) is similar to that described for the synthesis of compound 27 in Scheme 7.
Scheme 8
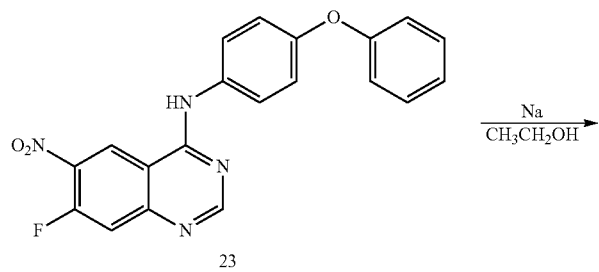

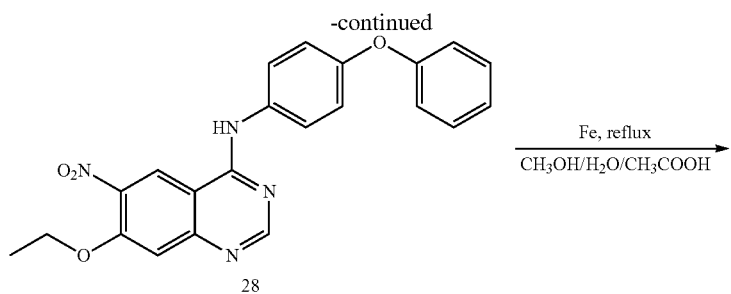
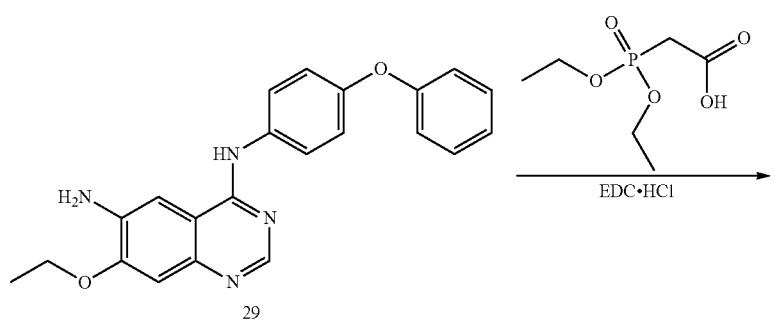
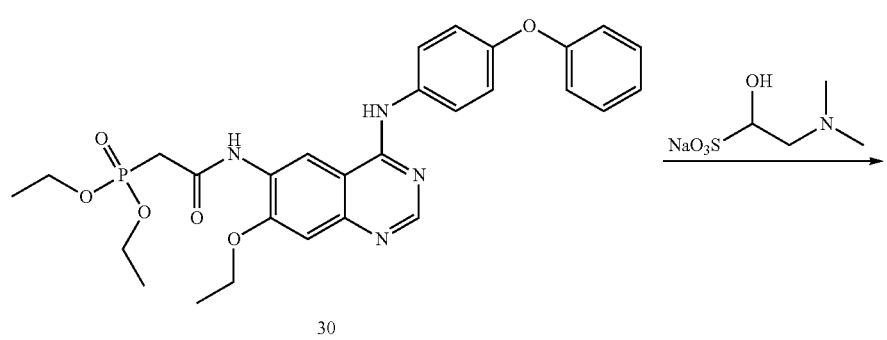
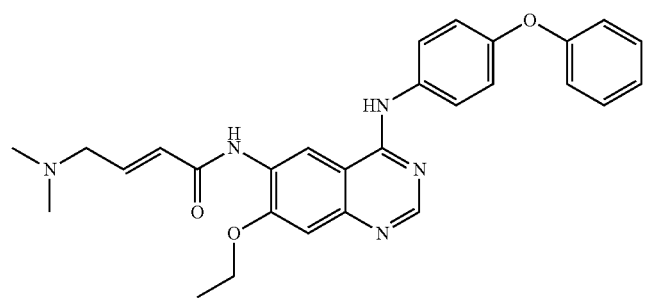

The synthesis of compound 35 (Scheme 9) is similar to that described for the synthesis of compound 27 in Scheme 7.
Scheme 9
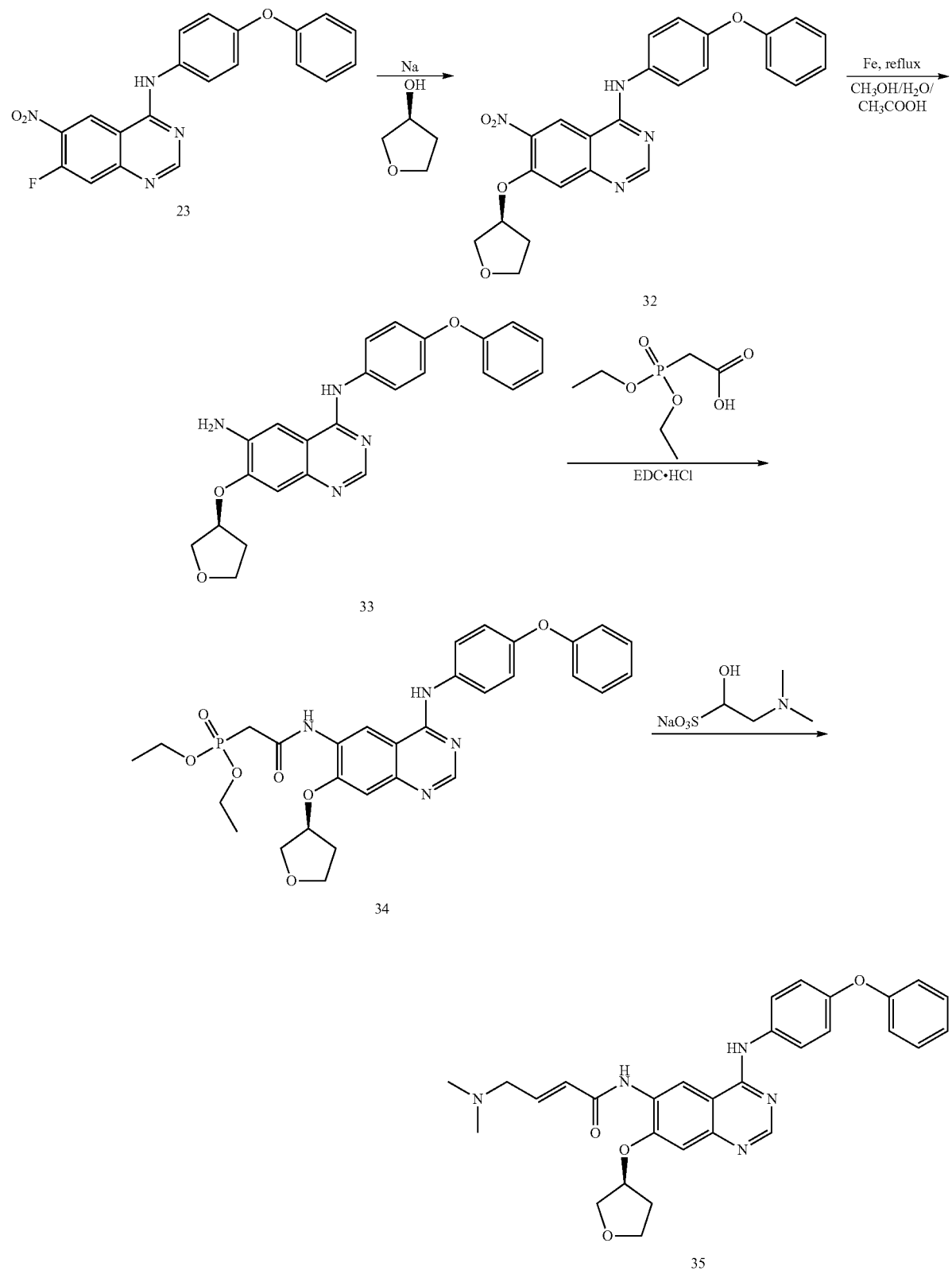

The synthesis of compound 36 is described in Scheme 10. The reaction of compound 25 with acryloyl chloride led to the preparation of compound 36.

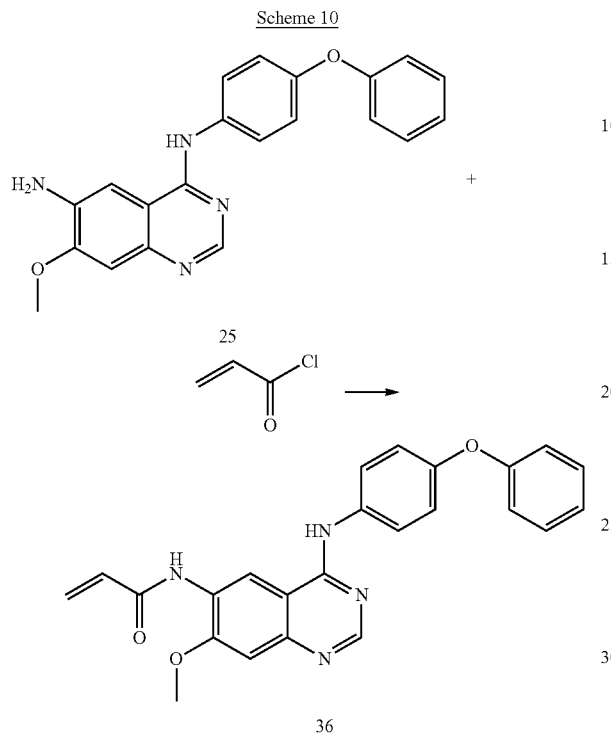

DESCRIPTION OF EMBODIMENTS

These detailed descriptions are presented for illustrative purposes only and are not intended as a restriction on the scope of the invention.

Proton NMR Spectra

Unless otherwise indicated, all $^1$H NMR spectra were run on a Varian series Mercury 300, 400 MHz instrument or a Bruker series 400 MHz instrument. Where so characterized, all observed protons are reported as parts-per-million (ppm) downfield from tetramethylsilane (TMS) or other internal reference in the appropriate solvent indicated.

Abbreviation

DMF means N,N-dimethylformamide.
DCM means dichloromethane.
DIPEA means diisopropyl ethylamine.
THF means tetrahydrofuran.
TEA means triethylamine.
EA means ethyl acetate.
EDC means 1-ethyl-3-(3-dimethylaminopropyl)carbodiimide.
EDC.HCl mean 1-ethyl-3-(3-dimethylaminopropyl)carbodiimide hydrogen chloride salt.
AST means aspartate aminotransferase.
ALT means alanine aminotransferase.
KI means Potassium Iodine.

EXAMPLE 1

Preparation of 4-chloro-7-fluoro-6-nitroquinazoline (Compound 19)

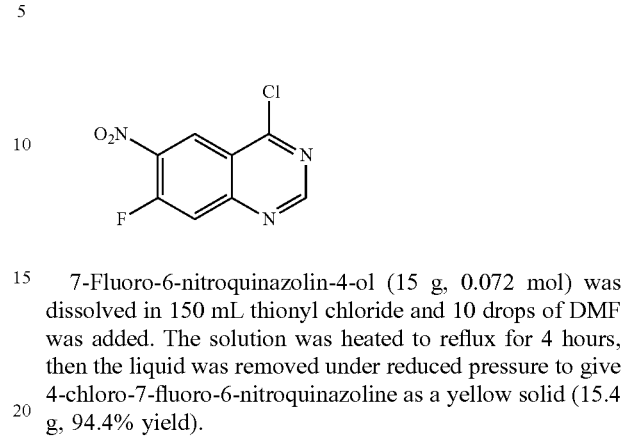

7-Fluoro-6-nitroquinazolin-4-ol (15 g, 0.072 mol) was dissolved in 150 mL thionyl chloride and 10 drops of DMF was added. The solution was heated to reflux for 4 hours, then the liquid was removed under reduced pressure to give 4-chloro-7-fluoro-6-nitroquinazoline as a yellow solid (15.4 g, 94.4% yield).

EXAMPLE 2

Preparation of 7-fluoro-6-nitro-N-(4-phenoxyphenyl)quinazolin-4-amine (Compound 23)

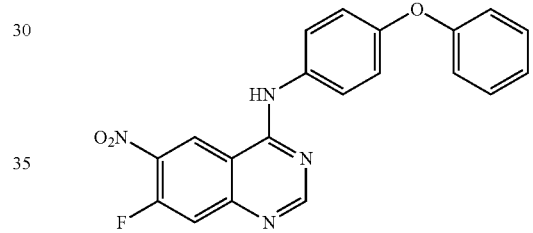

4-Chloro-7-fluoro-6-nitroquinazoline (10 g, 0.044 mol) was dissolved in 100 mL DCM, then a solution of 4-phenoxyaniline (8.96 g, 0.048 mol) in 200 mL isopropanol was added dropwise at 0° C. The solution was stirred at room temperature for one hour, and TEA (5.34 g, 0.052 mol) was added at 0° C. After stirring at room temperature for another 0.5 hour, and the yellow precipitate was filtered and washed with isopropanol (2×30 mL), H$_2$O (2×30 mL), and dried to give 7-fluoro-6-nitro-N-(4-phenoxy phenyl)quinazolin-4-amine as a yellow solid (15 g, 90.9% yield).

EXAMPLE 3

Preparation of 7-methoxy-6-nitro-N-(4-phenoxyphenyl)quinazolin-4-amine (Compound 24)

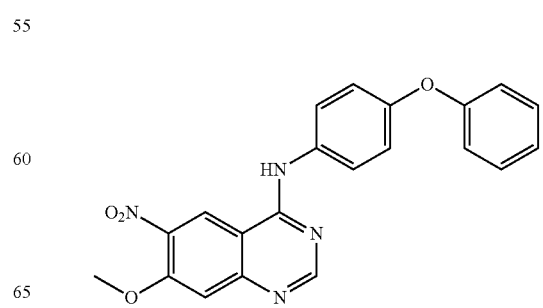

Sodium (1.18 g, 0.051 mol) was carefully dissolved in 100 mL anhydrous methanol to form a clear solution, then 7-fluoro-6-nitro-N-(4-phenoxyphenyl)quinazolin-4-amine (10 g, 0.026 mol) was added and stirred at 80° C. for 4 hours. The solution was concentrated under reduced pressure, and 50 mL H₂O was added. The precipitate was filtered and dried to give 7-methoxy-6-nitro-N-(4-phenoxyphenyl)quinazolin-4-amine as a yellow solid (9.2 g, 89.3% yield).

EXAMPLE 4

Preparation of 7-methoxy-N⁴-(4-phenoxyphenyl)quinazoline-4,6-diamine (Compound 25)

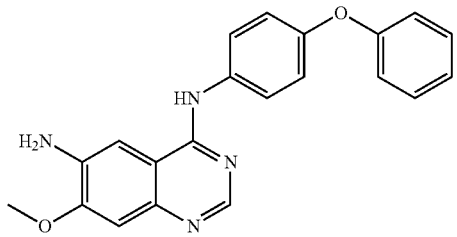 [SMILES: COc1cc2ncnc(Nc3ccc(Oc4ccccc4)cc3)c2cc1[N+](=O)[O-]]

7-Methoxy-6-nitro-N-(4-phenoxyphenyl)quinazolin-4-amine (6 g, 0.015 mol) and ammonium chloride (3.0 g, 0.056 mol) was dissolved in 200 mL methanol, 150 mL H₂O and 80 mL EA. The reaction was heated to 70° C. and iron (3.5 g, 0.062 mol) was added. The reaction was heated to reflux for 4 hours, filtered and concentrated under reduced pressure. The solid was collected and dried to give 7-methoxy-N⁴-(4-phenoxyphenyl)quinazoline-4,6-diamine as a grey solid (4.1 g, 74.1% yield).

EXAMPLE 5

Preparation of diethyl (2-((7-methoxy-4-((4-phenoxyphenyl)amino)quinazolin-6-yl)amino)-2-oxoethyl)phosphonate (Compound 26)

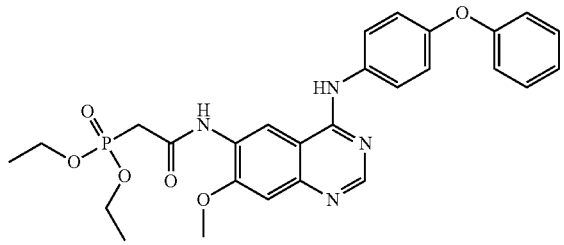 [SMILES: CCOP(=O)(CC(=O)Nc1cc2c(Nc3ccc(Oc4ccccc4)cc3)ncnc2cc1OC)OCC]

7-Methoxy-N⁴-(4-phenoxyphenyl)quinazoline-4,6-diamine (2 g, 5.59 mmol), 2-(diethoxyphosphoryl)acetic acid (1.42 g, 7.26 mmol) and EDC.HCl (2.1 g, 10.9 mmol) was added in 20 mL DMF, then DIPEA (1.44 g, 11.2 mmol) was added. The reaction solution was stirred at 50° C. for 4 hours and poured into 200 mL EA. The solution was washed with H₂O (3×100 mL), the organic layer was concentrated. Purification by flash silica gel chromatography afforded diethyl 2-(7-methoxy-4-(4-phenoxyphenylamino)quinazolin-6-ylamino)-2-oxoethylphosphonate as an off-white solid (1.5 g, 50.0% yield).

EXAMPLE 6

Preparation of (E)-4-(dimethylamino)-N-(7-methoxy-4-((4-phenoxyphenyl)amino)quinazolin-6-yl)but-2-enamide (Compound 27)

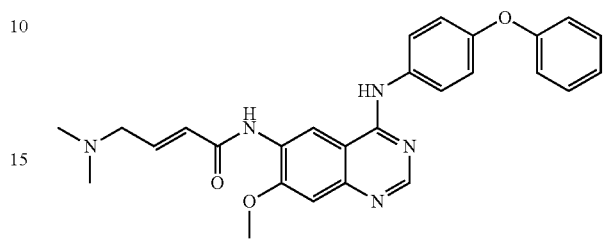

Diethyl 2-(7-methoxy-4-(4-phenoxyphenylamino)quinazolin-6-ylamino)-2-oxoethylphosphonate (1.5 g, 2.79 mmol) and sodium 2-(dimethylamino)-1-hydroxyethanesulfonate (1.1 g, 5.75 mmol) and LiCl (150 mg, 3.57 mmol) were added in 15 mL DMSO, then tert-BuOK (3 g, 26.7 mmol) was added at 0° C. The resulting solution was stirred at 50° C. for 2 hours, then poured into 150 mL EA and 150 mL H₂O. The organic layer was concentrated. Purification by flash silica gel chromatography gave (E)-4-(dimethylamino)-N-(7-methoxy-4-(4-phenoxyphenylamino)quinazolin-6-yl)but-2-enamide as off-white solid (280 mg, 21.3% yield). ¹H-NMR(CDCl₃, 400 MHz): δ9.10 (s,1H), 8.63 (s, 1H), 8.15 (s, 1H), 7.72-7.36 (m, 3H), 7.36-7.32 (m, 2H), 7.25 (s, 1H), 7.12-7.00 (m, 6H), 6.26-6.21 (m, 1H), 4.05 (s, 3H), 3.19 (m, 2H), 2.31 (s, 6H); LCMS: 469 [M−1]; Btk Kd: 2.2 nM.

EXAMPLE 7

Preparation of 7-ethoxy-6-nitro-N-(4-phenoxyphenyl)quinazolin-4-amine (Compound 28)

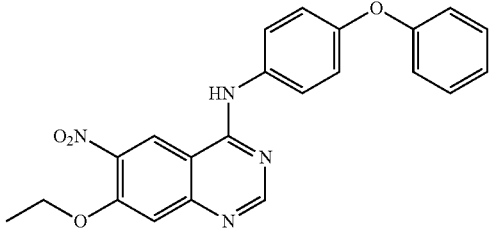

Sodium (1.18 g, 0.051 mol) was carefully dissolved in 100 mL anhydrous ethanol, then 7-fluoro-6-nitro-N-(4-phenoxyphenyl)quinazolin-4-amine (10 g, 0.026 mol) was added and stirred at 80° C. for 4 hours. The solution was concentrated under reduced pressure, and 50 mL H₂O was added. The solid precipitate was filtered and dried to give 7-ethoxy-6-nitro-N-(4-phenoxyphenyl)quinazolin-4-amine as a yellow solid (9.5 g, 88.9% yield).

EXAMPLE 8

Preparation of 7-ethoxy-N⁴-(4-phenoxyphenyl)quinazoline-4,6-diamine (Compound 29)

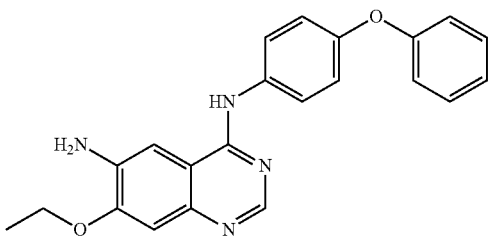 [SMILES: CCOc1cc2ncnc(Nc3ccc(Oc4ccccc4)cc3)c2cc1[N+](=O)[O-]]

7-Ethoxy-6-nitro-N-(4-phenoxyphenyl)quinazolin-4-amine (10 g, 0.025 mol) and ammonium chloride (5.0 g, 0.094 mol) was dissolved in a solution of 300 mL methanol, 150 mL H$_2$O and 100 mL EA. The reaction was heated to 70° C., then iron (11 g, 0.196 mol) was added. The reaction mixture was heated to reflux for 4 hours, cooled to room temperature, filtered and concentrated under reduced pressure. The filtrate was collected and dried to give 7-ethoxy-N⁴-(4-phenoxyphenyl)quinazoline-4,6-diamine as a grey solid (6.0 g, 64.8% yield).

EXAMPLE 9

Preparation of diethyl (2-((7-ethoxy-4-((4-phenoxyphenyl)amino)quinazolin-6-yl)amino)-2-oxoethyl)phosphonate (Compound 30)

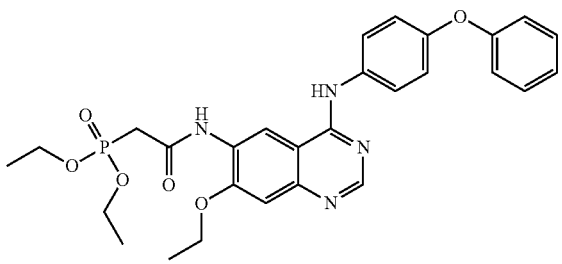 [SMILES: CCOc1cc2ncnc(Nc3ccc(Oc4ccccc4)cc3)c2cc1NC(=O)CP(=O)(OCC)OCC]

7-Ethoxy-N⁴-(4-phenoxyphenyl)quinazoline-4,6-diamine (400 mg, 1.07 mmol), 2-(diethoxyphosphoryl)acetic acid (274 mg, 1.4 mmol) and EDC.HCl (454 mg, 2.36 mmol) were added into 4 mL DMF. DIPEA (300 mg, 2.32 mmol) was added and the reaction stirred at 50° C. for 4 hours. The reaction solution was poured into 40 mL EA and washed with H$_2$O (3×40 mL). The organic layer was concentrated and purification by flash silica gel chromatography gave diethyl(2-((7-ethoxy-4-((4-phenoxyphenyl)amino)quinazolin-6-yl)amino)-2-oxoethyl)phosphonate as an off-white solid (250 mg, 42.3% yield).

EXAMPLE 10

Preparation of (E)-4-(dimethylamino)-N-(7-ethoxy-4-((4-phenoxyphenyl)amino)quinazolin-6-yl)but-2-enamide (Compound 31)

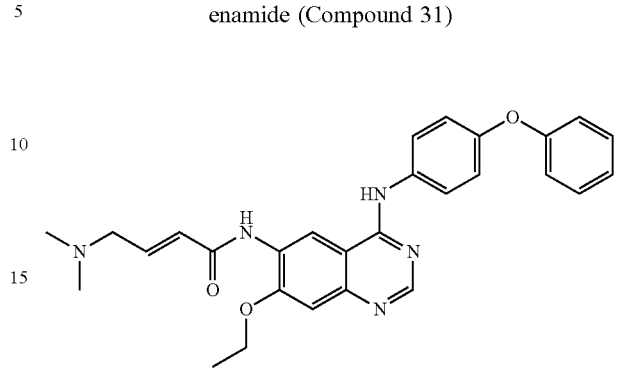

Diethyl 2-(7-ethoxy-4-(4-phenoxyphenylamino)quinazolin-6-ylamino)-2-oxoethylphosphonate (0.5 g, 0.91 mmol), sodium 2-(dimethylamino)-1-hydroxyethanesulfonate (0.35 g, 1.82 mmol) and LiCl (38 mg, 0.91 mmol) were added into 5 mL DMSO, then tert-BuOK (1 g, 8.91 mmol) was added at 0° C. The resulting solution was stirred at 50° C. for 2 hours. The reaction solution was poured into 50 mL EA and 50 mL H$_2$O. The organic layer was concentrated and purification by flash silica gel chromatography gave (E)-4-(dimethylamino)-N-(7-ethoxy-4-((4-phenoxyphenyl)amino)quinazolin-6-yl)but-2-enamide as an off-white solid (85 mg, 19.3% yield). $^1$H-NMR(CDCl$_3$, 400 MHz): δ1.57(t, J=6.8 Hz, 3H), 2.35(s, 6H), $^1$H-NMR(CDCl$_3$, 400 MHz): δ9.11 (s, 1H), 8.63 (s, 1H), 8.18 (s, 1H), 7.72-7.67 (m, 3H), 7.36-7.32 (m, 2H), 7.25 (s, 1H), 7.12-7.00 (m, 6H), 6.26 (d, J=15.2 Hz, 1H), 4.29 (q, J=6.8 Hz, 2H), 3.24-3.22 (m, 2H), 2.36 (s, 6H), 1.57 (t, J=6.8 Hz, 3H); LCMS: 483 [M−1]; Btk Kd: 2.6 nM.

EXAMPLE 11

Preparation of (S)-6-nitro-N-(4-phenoxyphenyl)-7-((tetrahydrofuran-3-yl)oxy)quinazolin-4-amine (Compound 32)

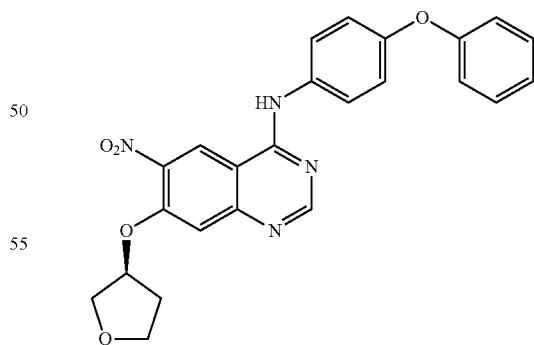

In an ice bath, sodium hydride (0.54 g, 60%, 0.013 mol) was carefully added into a solution of (S)-tetrahydrofuran-3-ol (0.98 g, 0.011 mol) in 35 ml anhydrous THF. The reaction was stirred at room temperature for 2 hours, then 7-fluoro-6-nitro-N-(4-phenoxyphenyl)quinazolin-4-amine (3.5 g, 0.009 mol) was added and stirred at 60° C. overnight. The solution was quenched with 1 mL H$_2$O and concentrated, and purification by flash silica gel chromatography gave (S)-6-nitro-N-(4-phenoxyphenyl)-7-((tetrahydrofuran-3-yl)oxy)quinazolin-4-amineas an off-white solid (0.84 g, 20.3% yield).

EXAMPLE 12

Preparation of (S)-N⁴-(4-phenoxyphenyl)-7-((tetrahydrofuran-3-yl)oxy)quinazoline-4,6-diamine (Compound 33)

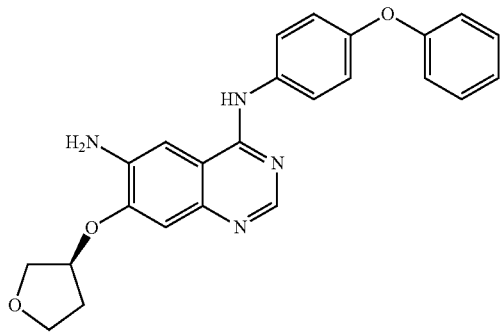 [SMILES: Nc1cc2c(Nc3ccc(Oc4ccccc4)cc3)ncnc2cc1O[C@H]1CCOC1]

(S)-7-(Cyclopentoxy)-6-nitro-N-(4-phenoxyphenyl)quinazolin-4-amine (0.8 g, 1.8 mmol) and ammonium chloride (0.8 g, 15.1 mmol) were added into a solution of 24 mL methanol, 15 mL H₂O and 8 mL EA. The reaction was heated to 70° C., then iron (0.8 g, 14.3 mmol) was added into the solution. The reaction mixture was heated to reflux for 4 hours. The resulting solution was filtered and concentrated. The filtrate was collected and dried to give (S)-N⁴-(4-phenoxyphenyl)-7-(tetrahydrofuran-3-yloxy)quinazoline-4,6-diamine as a grey solid (0.60 g, 80.5% yield).

EXAMPLE 13

Preparation of (S)-diethyl (2-oxo-2-((4-((4-phenoxyphenyl)amino)-7-((tetrahydrofuran-3-yl)oxy)quinazolin-6-yl)amino)ethyl)phosphonate (Compound 34)

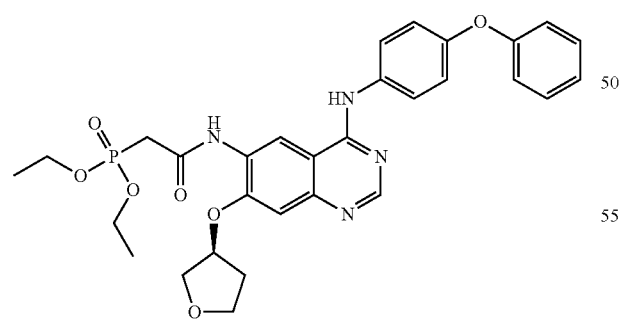

(S)-N⁴-(4-Phenoxyphenyl)-7-(tetrahydrofuran-3-yloxy)quinazoline-4,6-diamine (0.6 g, 1.45 mmol), 2-(diethoxyphosphoryl)acetic acid (0.35 g, 1.78 mmol) and EDC.HCl (0.6 g, 3.13 mmo) were added into 6 mL DMF, then DIPEA (0.4 g, 3.1 mmol) was added. The reaction was stirred at 50° C. for 4 hours before was poured into 50 mL EA. It was washed with 3×50 mL H₂O, the organic layer was concentrated and purification by flash silica gel chromatography gave (S)-diethyl 2-oxo-2-(4-(4-phenoxyphenylamino)-7-(tetrahydrofuran-3-yloxy)quinazolin-6-ylamino)ethylphosphonate as an off-white solid (0.35 g, 40.7% yield).

EXAMPLE 14

Preparation of (S,E)-4-(dimethylamino)-N-(4-((4-phenoxyphenyl)amino)-7-((tetrahydrofuran-3-yl)oxy)quinazolin-6-yl)but-2-enamide (Compound 35)

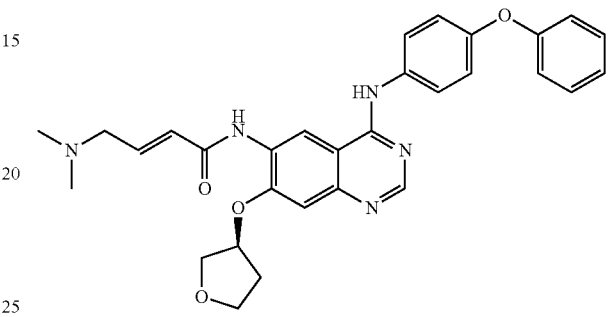

(S)-Diethyl-2-oxo-2-(4-(4-phenoxyphenylamino)-7-(tetrahydrofuran-3-yloxy)quinazolin-6-ylamino)ethylphosphonate (0.4 g, 0.67 mmol), sodium 2-(dimethylamino)-1-hydroxyethanesulfonate (0.2 g, 1.05 mmol) and LiCl (40 mg, 0.95 mmol) were added into 4 mL DMSO, then t-BuOK (0.8 g, 7.1 mmol) was added at 0° C. degree. The reaction was stirred at 50° C. for 2 hours before poured into 50 mL EA and 50 mL H₂O. The organic layer was concentrated and purification by flash silica gel chromatography gave (S,E)-4-(dimethylamino)-N-(4-(4-phenoxyphenylamino)-7-(tetrahydrofuran-3-yloxy)quinazolin-6-yl)but-2-enamide as a white solid (18 mg, 5.1% yield). ¹H-NMR(CDCl₃, 400 MHz): δ2.21-2.30(m, 1H), 2.32(s, 6H), δ9.16 (s, 1H), 8.63 (s, 1H), 8.07 (s, 1H), 7.68-7.66 (m, 2H), 7.36-7.32 (m, 2H), 7.58(s, 1H), 7.32-7.36(m, 2H), 7.20 (s, 1H), 7.12-7.03 (m, 6H), 6.24-6.20 (m, 1H), 5.19 (m, 1H), 4.21-4.16(m, 1H), 4.10-4.06 (m, 2H), 3.95-3.90 (m, 1H), 3.18-3.17 (m, 2H), 2.50-2.39 (m, 1H), 2.32 (s, 6H), 2.30-2.21 (m, 1H).

EXAMPLE 15

Preparation of N-(7-methoxy-4-((4-phenoxyphenyl)amino)quinazolin-6-yl)acrylamide (Compound 36).

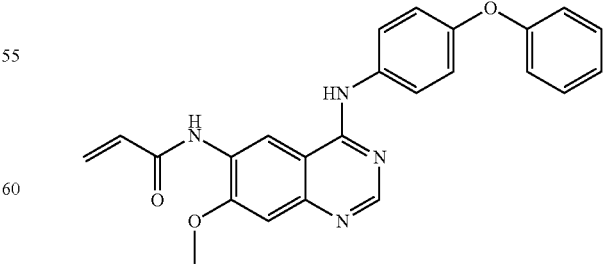

7-Methoxy-N⁴-(4-phenoxyphenyl)quinazoline-4,6-diamine (0.5 g, 1.39 mmol), and TEA (0.42 g, 4.16 mmol) were added in a solution of 25 mL dioxane and 25 mL DCM, then acryloyl chloride (0.3 g, 3.29 mmol) was added dropwise at 0° C. The reaction solution was stirred at room temperature for 2 hours before was poured into 100 mL DCM and 100 mL H$_2$O. The organic layer was concentrated and purification by flash silica gel chromatography gave N-(7-methoxy-4-(4-phenoxyphenylamino)quinazolin-6-yl)acrylamide as an off-white solid (180 mg, 31.3% yield). $^1$H-NMR(CDCl$_3$, 400 MHz): δ9.13 (s, 1H), 8.64 (s, 1H), 8.18 (s, 1H), 7.69-7.66 (m, 2H), 7.58 (s, 1H), 7.36-7.32 (m, 2H), 7.26 (s, 1H), 7.12-7.03 (m, 5H), 6.50 (d, J=16.8 Hz, 1H), 6.36 (dd, J =10.4 Hz, J=16.8 Hz, 1H), 5.87 (d, J =10.4 Hz, 1H), 4.06 (s, 3H).

EXAMPLE 16

Preparation of N-(7-methoxy-4-((4-phenoxyphenyl)amino)quinazolin-6-yl)acrylamide (Compound 37)

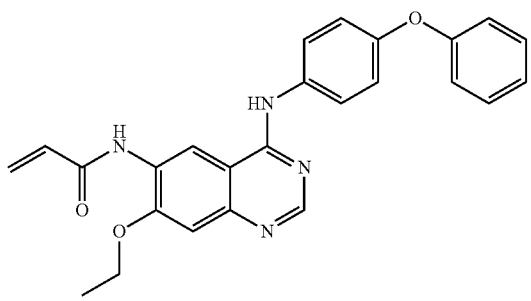 [SMILES: C=CC(=O)Nc1cc2c(Nc3ccc(Oc4ccccc4)cc3)ncnc2cc1OCC]

7-Methoxy-N$^4$-(4-phenoxyphenyl)quinazoline-4,6-diamine(0.5 g, 1.39 mmol), and TEA (0.42 g, 4.16 mmol) were added in a solution of 25 mL dioxane and 25 mL DCM, then acryloyl chloride7-Ethoxy-N$^4$-(4-phenoxyphenyl)quinazoline-4,6-diamine (0.5 g, 1.34 mmol), and TEA (1.2 g, 11.8 mmol) were added into a solution of 20 mL dioxane and 20mL DCM, then acryloyl chloride (245 mg, 2.69 mmol) was added at 0° C. The resulting solution was stirred at room temperature for 2 hours and was poured into 100 mL DCM and 100 mL H$_2$O. The organic layer was concentrated and purification by flash silica gel chromatography gave N-(7-ethoxy-4-(4-phenoxyphenylamino)quinazolin-6-yl)acrylamide as an off-white solid (59 mg, 10.3% yield). $^1$H-NMR (CDCl$_3$, 400 MHz): δ9.14 (s, 1H), 8.64 (s, 1H), 8.20 (s, 1H), 7.69-7.65 (m, 2H), 7.48 (s, 1H), 7.37-7.32 (m, 2H), 7.26 (s, 1H), 7.13-7.04 (m, 5H), 6.50 (dd, J=16.8 Hz, J=1.2 Hz, 1H), 6.37(dd, J=10 Hz, J=16.8 Hz, 1H), 5.87 (dd, J=10 Hz, J=1.2 Hz, 1H), δ4.32 (q, J=6.8 Hz, 2H), 1.58(t, J=6.8 Hz, 3H).

EXAMPLE 17

Preparation of (S)-N-(4-((4-phenoxyphenyl)amino)-7-((tetrahydrofuran-3-yl)oxy)quinazolin-6-yl)acrylamide (Compound 38)

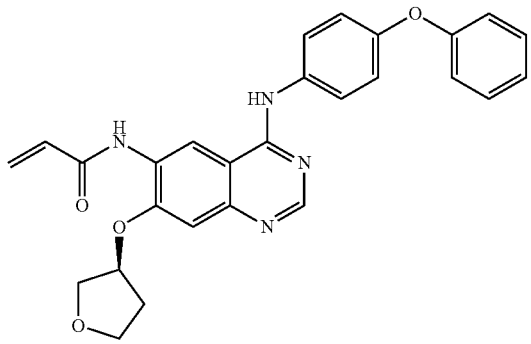 [SMILES: C=CC(=O)Nc1cc2c(Nc3ccc(Oc4ccccc4)cc3)ncnc2cc1O[C@H]1CCOC1]

(S)-N$^4$-(4-Phenoxyphenyl)-7-(tetrahydrofuran-3-yloxy)quinazoline-4,6-diamine (0.6 g, 1.45 mmol) and TEA (0.44 g, 4.36 mmol) were added into a solution of 25 mL dioxane and 25 mL DCM, then acryloyl chloride (0.26 g, 2.87 mmol) was added at 0° C. The resulting solution was stirred at room temperature for 2 hours and was poured into 100 ml DCM and 100 mL H$_2$O. The organic layer was concentrated purification by flash silica gel chromatography gave (S)-N-(4-(4-phenoxyphenylamino)-7-(tetrahydrofuran-3-yloxy)quinazolin-6-yl)acrylamide as an off-white solid (80 mg, 11.8% yield). $^1$H-NMR(CDCl$_3$, 400 MHz): δ9.17 (s, 1H), 8.64 (s, 1H), 8.12 (s, 1H), 7.68-7.65 (m, 2H), 7.37-7.33 (m, 2H), 7.49 (s, 1H), 7.20 (s, 1H), 7.13-7.04 (m, 5H), 6.50 (dd, J=16.4 Hz, J=1.2 Hz, 1H), 6.36 (dd, J=10 Hz, J=16.4 Hz, 1H), 5.87 (dd, J=10 Hz, J=1.2 Hz, 1H), 5.20-5.17 (m, 1H), 4.18-4.15 (m, 1H), 4.11-4.03 (m, 2H), 3.97-3.92 (m, 1H), 2.48-2.39 (m, 1H), 2.29-2.23 (m, 1H).

EXAMPLE 18

Preparation of (E)-4-(dimethylamino)-N-(4-((4-(4-fluorophenoxy)phenyl)amino)-7-methoxyquinazolin-6-yl)but-2-enamide (Compound 39)

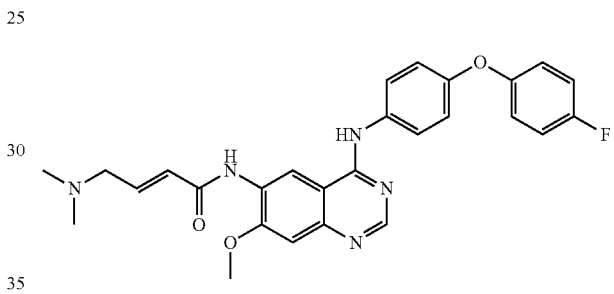

Step 1: 4-Chloro-7-fluoro-6-nitroquinazoline (1.00 equiv) is dissolved in 100 mL DCM, then a solution of 4-(4-fluorophenoxy)aniline (1.05 equiv) in 200 mL isopropanol is added dropwise at 0° C. The solution is stirred at room temperature for one hour, and TEA (1.10 equiv) is added at 0° C. After stifling at room temperature for another 0.5 hour, and the precipitate is filtered, washed with isopropanol and dried to give 7-fluoro-N-(4-(4-fluorophenoxy)phenyl)-6-nitroquinazolin-4-amine.

Step 2: Sodium (2.00 equiv) is carefully dissolved in 100 mL anhydrous methanol to form a clear solution, then 7-fluoro-N-(4-(4-fluorophenoxy)phenyl)-6-nitroquinazolin-4-amine (1.00 equiv) is added and stirred at 80° C. for 4 hours. The solution is concentrated under reduced pressure, and H$_2$O is added. The precipitate is filtered and dried to give N-(4-(4-fluorophenoxy)phenyl)-7-methoxy-6-nitroquinazolin-4-amine.

Step 3: N-(4-(4-fluorophenoxy)phenyl)-7-methoxy-6-nitroquinazolin-4-amine (1.00 equiv) and ammonium chloride (3.72 equiv) are dissolved in a mixture of methanol, H$_2$O and EA (v/v/v, 1:1:1). The reaction is heated to 70° C. and iron (5.0 equiv) is added. The reaction is heated to reflux for 4 hours, filtered and concentrated under reduced pressure. The solid is collected and dried to give N$^4$-(4-(4-fluorophenoxy)phenyl)-7-methoxyquinazoline-4,6-diamine.

Step 4: N$^4$-(4-(4-fluorophenoxy)phenyl)-7-methoxyquinazoline-4,6-diamine (1.00 equiv), 2-(diethoxyphosphoryl)acetic acid (1.3 equiv) and EDC.HCl (1.95 equiv) are added in 20 mL DMF, then DIPEA (2.00 equiv) is added. The reaction solution is stirred at 50° C. for 4 hours and poured into 200 mL EA. The solution is washed with H$_2$O, and the organic layer is concentrated. Purification by flash silica gel chromatography affords diethyl (2-((4-((4-(4-fluorophenoxy)phenyl)amino)-7-methoxyquinazolin-6-yl) amino)-2-oxoethyl)phosphonate.

Step 5: Diethyl (2-((4-((4-(4-fluorophenoxy)phenyl) amino)-7-methoxyquinazolin-6-yl)amino)-2-oxoethyl) phosphonate (1.00 equiv) and sodium 2-(dimethylamino)-1-hydroxyethanesulfonate (2.06 equiv) and LiCl (1.28 equiv) are added in DMSO, then tert-BuOK (9.5 equiv) is added at 0° C. The resulting solution is stirred at 50° C. for 2 hours, then is poured into EA and H$_2$O. The organic layer is concentrated. Purification by flash silica gel chromatography affords (E)-4-(dimethylamino)-N-(4-((4-(4-fluorophenoxy)phenyl)amino)-7-methoxyquinazolin-6-yl)but-2-enamide.

EXAMPLE 19

Preparation of (E)-N-(4-((4-(3-cyanophenoxy)phenyl)amino)-7-methoxyquinazolin-6-yl)-4-(dimethylamino)but-2-enamide (Compound 40)

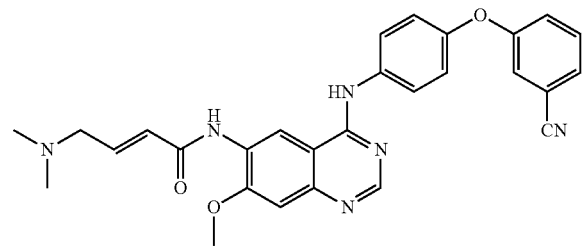

The title compound is synthesized according to Scheme 7, using the similar procedure described in Example 6 or example 18. Staring material 3-(4-aminophenoxy)benzonitrile is used.

EXAMPLE 20

Preparation of (E)-4-(dimethylamino)-N-(7-methoxy-4-((4-(3-(trifluoromethyl)phenoxy)phenyl) amino)quinazolin-6-yl)but-2-enamide (Compound 41)

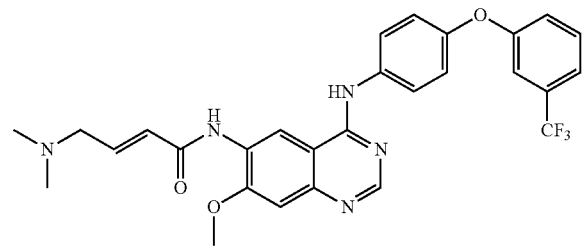 [SMILES: COc1cc2ncnc(Nc3ccc(Oc4cccc(C#N)c4)cc3)c2cc1NC(=O)/C=C/CN(C)C]

The title compound is synthesized according to Scheme 7, using the similar procedure described in Example 6 or example 18. Staring material 4-(3-(trifluoromethyl)phenoxy)aniline is used.

EXAMPLE 21

Preparation of (E)-4-(dimethylamino)-N-(7-methoxy-4-((4-(pyridin-2-yloxy)phenyl)amino)quinazolin-6-yl)but-2-enamide (Compound 42).

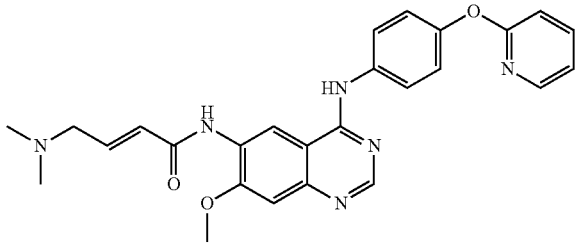 [SMILES: COc1cc2ncnc(Nc3ccc(Oc4ccccn4)cc3)c2cc1NC(=O)/C=C/CN(C)C]

The title compound is synthesized according to Scheme 7, using the similar procedure described in Example 6 or example 18. Staring material 4-(pyridin-2-yloxy)aniline is used.

EXAMPLE 22

Preparation of (E)-N-(4-((4-(3,4-dichlorophenoxy) phenyl)amino)-7-methoxyquinazolin-6-yl)-4-(dimethylamino)but-2-enamide (Compound 43)

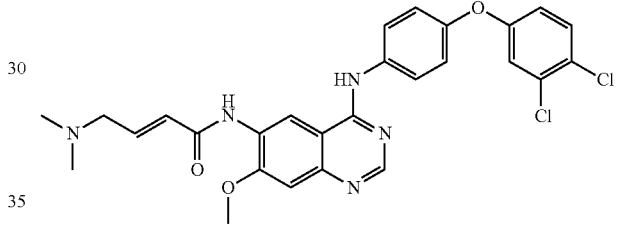

The title compound is synthesized according to Scheme 7, using the similar procedure described in Example 6 or example 18. Staring material 4-(3,4-dichlorophenoxy)aniline is used.

Biological Assays:

As stated herein before, the compounds defined in the present invention possess anti-proliferation activity. These properties may be assessed, for example, using one or more of the procedures set out below:

An in vitro assay which determines the ability of a test compound to inhibit Btk.

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17× PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1× PBS, 0.05% Tween 20). The beads were then resuspended in elution buffer (1× PBS, 0.05% Tween 20, 0.5 µM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Kds were determined using a compound top concentration=10,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation: Response=Background+(Signal−Background)/(1+ ($Kd^{Hill\ Slope}/Dose^{Hill\ Slope}$)). The Hill Slope was set to −1. Curves were fitted using a non-linear least square fit with the Levenberg-Marquardt algorithm.

The following Table 1 lists compounds representative of the invention and their corresponding inhibitory activity against Btk.

TABLE 1

| No | Btk, Kd (nM) |
| --- | --- |
| Compound 27 | 2.2 |
| Compound 31 | 2.6 |
| Compound 35 | <100 |
| Compound 36 | 2.3 |
| Compound 37 | 1.2 |
| Compound 38 | <100 |

Btk Ramos Cellular Assay

Ramos cells were grown in suspension in T225 flasks, spun down, resuspended in 50 mL serum-free media and incubated for 1 hour. Compound was added to Ramos cells in serum free media to a final concentration of 1, 0.1, 0.01, or 0.001 µM. Ramos cells were incubated with compound for 1 hour, washed again and resuspended in 100 µL serum-free media. Cells were then stimulated with 1 µg of goat F(ab')2 Anti-Human IgM and incubated on ice for 10 minutes to activate B cell receptor signaling pathways. After 10 minutes, the cells were washed once with PBS and then lysed on ice with Invitrogen Cell Extraction buffer. Sixteen µg total protein from lysates was loaded on gels and blots were probed for phosphorylation of the Btk substrate PLC gamma.2. For example, compound 27 and compound 31 showed inhibition of Btk signaling in Ramos cellular assay at $IC_{50}$ less than 100 nM.

What is claimed is:

1. A compound according to Formula I:

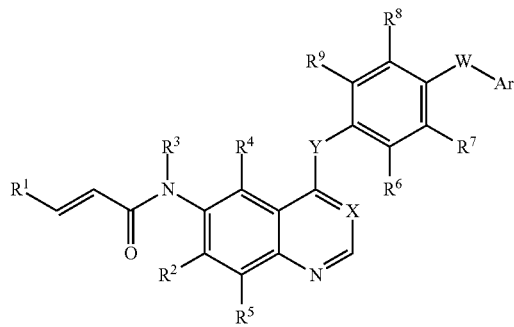

I or a pharmaceutically acceptable salt, solvate, stereoisomer or a tautomer thereof, wherein X is N;

Y is O, S, or NH;

W is $CHR^3$, O, S, NH, C(O), S(O), or $S(O)_2$;

Ar is $C_6$-$C_{12}$ aryl, 5-12 membered heteroaryl, $C_3$-$C_{12}$ cycloalkyl, or 3-12 membered heteroalicyclic, and Ar is optionally substituted by one or more $R^{10}$) groups;

$R^1$ is hydrogen, —$(CHR^3)_mN(O)R^{11}R^{12}$, —$(CHR^3)_m NR^{11}R^{12}$, or —$(CHR^3)_m R^{13}$;

$R^2$ is $OCH_3$, or $OCH_2CH_3$;

each $R^3$ is independently hydrogen or $C_1$-$C_6$ alkyl;

$R^4$, $R^5$, $R^6$, $R^7$, $R^8$ and $R^9$ are independently hydrogen, $C_1$-$C_6$ alkyl, $C_1$-$C_6$ alkoxy, F, Cl, CN, or $CF_3$;

each $R^{10}$ is independently halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, —$NR^{15}R^{16}$, —$(CR^{17}R^{18})_nOR^{15}$, CN, —$C(O)R^{15}$, —$O(CO)R^{15}$, —$O(CR^{17}R^{18})_nR^{15}$, —$OCR^{17}R^{18}(CR^{17}R^{18})_nNR^{15}R^{16}$, —$OCR^{17}R^{18}(CR^{17}R^{18})_nOR^{15}$, —$NR^{15}C(O)R^{16}$, —$(CR^{17}R^{18})_nC(O)OR^{15}$, —$(CR^{17}R^{18})_nNR^{15}R^{16}$, —$NR^{15}(CO)$—$NR^{15}R^{16}$, —$NR^{15}S(O)_pR^{16}$, —$S(O)_tR^{15}$, or —$S(O)_2NR^{15}R^{16}$, wherein two $R^{10}$ groups on adjacent atoms of Ar may, together with the adjacent atoms to which two $R^{10}$ groups are bound, be combined to form a $C_6$-$C_{12}$ aryl, 5-12 membered heteroaryl, $C_3$-$C_{12}$ cycloalkyl or 3-12 membered heteroalicyclic;

$R^{11}$ and $R^{12}$ are independently hydrogen, $C_1$-$C_6$ alkyl, or —$CR^{17}R^{18}(CR^{17}R^{18})_nOR^{15}$;

$R^{13}$ is morpholine, piperidine, piperazine, piperazine-N ($C_1$-$C_6$ alkyl), or pyrrolidine, and each hydrogen in $R^{13}$ is optionally substituted by one or more $C_1$-$C_6$ alkyl, $C_1$-$C_6$ alkoxy, halogen, OH, $NH_2$, NH($C_1$-$C_6$ alkyl), or N($C_1$-$C_6$ alkyl)$_2$;

each $R^{15}$, $R^{16}$, $R^{17}$, and $R^{18}$ is independently hydrogen, $C_1$-$C_6$alkyl; $C_6$-$C_{12}$ aryl, 5-12 membered heteroaryl, $C_3$-$C_{12}$ cycloalkyl or 3-12 membered heteroalicyclic; or any two of $R^{15}$, $R^{16}$, $R^{17}$, and $R^{18}$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^{15}$, $R^{16}$, $R^{17}$, and $R^{18}$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

each m is independently 1, 2, or 3;

each n is independently 0, 1, 2, 3, or 4;

each p is independently 1 or 2; and each t is independently 0, 1, or 2.

2. The compound of claim 1 or a pharmaceutically acceptable salt thereof, wherein Y is NH, and W is O.

3. The compound of claim 1 or a pharmaceutically acceptable salt thereof, wherein $R^1$ is H, $CH_2NR^{11}R^{12}$, or $CH_2$—N-piperidine.

4. The compound of claim 1 or a pharmaceutically acceptable salt thereof, wherein $R^4$, $R^5$, $R^6$, $R^7$, $R^8$ and $R^9$ are independently selected from the group consisting of hydrogen, $CH_3$, $OCH_3$, F, Cl, CN, and $CF_3$.

5. A compound according to Formula II:

II or a pharmaceutically acceptable salt, solvate, stereoisomer or tautomer thereof, wherein
- $R^1$ is hydrogen, $-(CHR^3)_m N(O)R^{11}R^{12}$, $-(CHR^3)_m NR^{11}R^{12}$, or $-(CHR^3)_m R^{13}$;
- $R^2$ is F, Cl, CN, $CF_3$, or $OR^{14}$;
- each $R^3$ is independently hydrogen or $C_1$-$C_6$ alkyl;
- $R^8$ is hydrogen, $C_1$-$C_6$ alkyl, $C_1$-$C_6$ alkoxy, F, Cl, CN, or $CF_3$;
- $R^{11}$ and $R^{12}$ are independently hydrogen, $C_1$-$C_6$ alkyl, or $-CR^{17}R^{18}(CR^{17}R^{18})_n OR^{15}$;
- $R^{13}$ is morpholine, piperidine, piperazine, piperazine-N ($C_1$-$C_6$ alkyl), or pyrrolidine, and each hydrogen in $R^{13}$ is optionally substituted by one or more $C_1$-$C_6$ alkyl, $C_1$-$C_6$ alkoxy, halogen, OH, $NH_2$, $NH(C_1$-$C_6$ alkyl), or $N(C_1$-$C_6$ alkyl)$_2$;
- $R^{14}$ is $C_1$-$C_6$ alkyl, $-CR^{17}R^{18}(CR^{17}R^{18})_n OR^{15}$, or tetrahydrofuran-3-yl;
- each $R^{15}$, $R^{16}$, $R^{17}$, and $R^{18}$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^{15}$, $R^{16}$, $R^{17}$, and $R^{18}$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^{15}$, $R^{16}$, $R^{17}$, and $R^{18}$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;
- each $R^{19}$, $R^{20}$, $R^{22}$ and $R^{23}$ is independently hydrogen, halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, $-NR^{15}R^{16}$, $-(CR^{17}R^{18})_n OR^{15}$, CN, $-C(O)R^{15}$, $-O(CO)R^{15}$, $-O(CR^{17}R^{18})_n R^{15}$, $-OCR^{17}R^{18}(CR^{17}R^{18})_n NR^{15}R^{16}$, $-OCR^{17}R^{18}(CR^{17}R^{18})_n OR^{15}$, $-NR^{15}C(O)R^{16}$, $-(CR^{17}R^{18})_n C(O)OR^{15}$, $-(CR^{17}R^{18})_n NR^{15}R^{16}$, $-NR^{15}(CO)-NR^{15}R^{16}$, $-NR^{15}S(O)_p R^{16}$, $-S(O)_t R^{15}$, and $-S(O)_2 NR^{15}R^{16}$;
- $R^{21}$ is halogen, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, $-NR^{15}R^{16}$, $-(CR^{17}R^{18})_n OR^{15}$, CN, $-C(O)R^{15}$, $-O(CO)R^{15}$, $-O(CR^{17}R^{18})_n R^{15}$, $-OCR^{17}R^{18}(CR^{17}R^{18})_n NR^{15}R^{16}$, $-OCR^{17}R^{18}(CR^{17}R^{18})_n OR^{15}$, $-NR^{15}C(O)R^{16}$, $-(CR^{17}R^{18})_n C(O)OR^{15}$, $-(CR^{17}R^{18})_n NR^{15}R^{16}$, $-NR^{15}(CO)-NR^{15}R^{16}$, $-NR^{15}S(O)_p R^{16}$, $-S(O)_t R^{15}$, and $-S(O)_2 NR^{15}R^{16}$;
- each m is independently 1, 2, or 3;
- each n is independently 0, 1, 2, 3, or 4;
- each p is independently 1 or 2; and
- each t is independently 0, 1, or 2.

6. The compound of claim 5 or a pharmaceutically acceptable salt thereof, wherein $R^1$ is H or $CH_2N(C_1$-$C_6$ alkyl)$_2$.

7. The compound of claim 5 or a pharmaceutically acceptable salt thereof, wherein $R^2$ is $OCH_3$, $OCH_2CH_3$, or tetrahydrofuran-3-yloxy.

8. The compound of claim 5 or a pharmaceutically acceptable salt thereof, wherein $R^8$ is hydrogen, F, Cl, CN, or $CF_3$.

9. A compound, or its pharmaceutically acceptable salt, solvate, stereoisomer or tautomer thereof, wherein the compound is selected from the group consisting of:
- (E)-4-(dimethylamino)-N-(7-methoxy-4((4-phenoxypheny)amino)quinazolin-6-yl)but-2-enamide;
- (E)-4-(dimethylamino)-N-(7-ethoxy-4((4-phenoxyphenyl)amino)quinazolin-6-yl)but-2-enamide;
- (S,E)-4-(dimethylamino)-N-(4((4-phenoxyphenyl)amino)-7-((tetrahydrofuran-3-yl)oxy)quinazolin-6-yl)but-2-enamide;
- (E)-4-(dimethylamino)-N-(4-((4-(4-fluorophenoxy)phenyl)amino)-7-methoxyquinazolin-6-yl)but-2-enamide;
- (E)-N-(4-((4-(3-cyanophenoxy)phenyl)amino)-7-methoxyquinazolin-6-yl)-4-(dimethylamino)but-2-enamide;
- (E)-4-(dimethylamino)-N-(7-methoxy-4-((4-(pyridin-2-yloxy)phenyl)amino)quinazolin-6-yl)but-2-enamide;
- (E)-N-(4-((4-(3,4-dichlorophenoxy)phenyl)amino)-7-methoxyquinazolin-6-yl)-4-(dimethylamino)but-2-enamide;
- (E)-4-(diethylamino)-N-(7-methoxy-4-((4-phenoxyphenyl)amino)quinazolin-6-yl)but-2-enamide;
- (E)-4-(diethylamino)-N-(4-((4-phenoxyphenyl)amino)quinazolin-6-yl)but-2-enamide;
- (E)-N-(4-((4-phenoxyphenyl)amino)quinazolin-6-yl)-4-(piperidin-1-yl)but-2-enamide;
- (E)-N-(7-methoxy-4-((4-phenoxyphenyl)amino)quinazolin-6-yl)-4-(piperidin-1-yl)but-2-enamide;
- N-(7-methoxy-4-((4-phenoxyphenyl)amino)quinazolin-6-yl)acrylamide;
- N-(7-ethoxy-4-((4-phenoxyphenyl)amino)quinazolin-6-yl)acrylamide; and
- (S)-N-(4-((4-phenoxyphenyl)amino)-7-((tetrahydrofuran-3-yl)oxy)quinazolin-6-yl)acrylamide.

10. A pharmaceutical composition comprising a compound of claim 1 or a pharmaceutically acceptable salt thereof and a pharmaceutically acceptable carrier.

* * * * *